United States Patent
Wang et al.

(10) Patent No.: US 11,124,558 B2
(45) Date of Patent: Sep. 21, 2021

(54) USE OF TETRANECTIN AND PEPTIDE AGONISTS TO TREAT INFLAMMATORY DISEASES

(71) Applicant: The Feinstein Institutes for Medical Research, Manhasset, NY (US)

(72) Inventors: Haichao Wang, Edison, NJ (US); Wei Li, Plainview, NY (US); Jianhua Li, New York, NY (US); Kevin J. Tracey, Old Greenwich, CT (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 0 days.

(21) Appl. No.: 16/617,811

(22) PCT Filed: Jun. 4, 2018

(86) PCT No.: PCT/US2018/035821
§ 371 (c)(1),
(2) Date: Nov. 27, 2019

(87) PCT Pub. No.: WO2018/223118
PCT Pub. Date: Dec. 6, 2018

(65) Prior Publication Data
US 2020/0190159 A1 Jun. 18, 2020

Related U.S. Application Data

(60) Provisional application No. 62/514,085, filed on Jun. 2, 2017.

(51) Int. Cl.
| | | |
|---|---|---|
| *C07K 14/705* | (2006.01) | |
| *A61P 7/00* | (2006.01) | |
| *A61P 29/00* | (2006.01) | |
| *C07K 7/08* | (2006.01) | |
| *A61K 38/00* | (2006.01) | |

(52) U.S. Cl.
CPC ............ *C07K 14/7056* (2013.01); *A61P 7/00* (2018.01); *A61P 29/00* (2018.01); *C07K 7/08* (2013.01); *A61K 38/00* (2013.01)

(58) Field of Classification Search
CPC ....... A61K 38/00; A61K 38/178; A61P 29/00; A61P 7/00; C07K 14/7056; C07K 7/08
See application file for complete search history.

(56) References Cited

U.S. PATENT DOCUMENTS

| | | | |
|---|---|---|---|
| 5,064,942 A | 11/1991 | Duhl Clemmensen et al. | |
| 7,820,622 B2* | 10/2010 | Ottow ................ | C07K 14/4726 514/16.6 |
| 8,791,063 B2* | 7/2014 | Bader ..................... | A61P 31/04 514/1.4 |
| 9,187,550 B2* | 11/2015 | Bader ....................... | A61P 7/00 |
| 2010/0028995 A1 | 2/2010 | Graversen et al. | |
| 2011/0245592 A1* | 10/2011 | Schoolcraft .......... | G01N 33/689 600/34 |
| 2013/0231273 A1* | 9/2013 | Bader .................... | C12N 15/62 514/1.4 |
| 2020/0376028 A1* | 12/2020 | Palti .......................... | A61P 3/10 |

OTHER PUBLICATIONS

Hotchkiss et al. Immunosuppression in sepsis: a novel understanding of the disorder and a new therapeutic approach. Lancet Infect Dis, 2013. vol. 13, No. 3, pp. 260-268. (Year: 2013).*
International Search Report and Written Opinion dated Oct. 29, 2018 from PCT International Patent Application No. PCT/US2018/035821.
Tsao et al., "Coagulation Abnormalities in Sepsis," Acta Anaesthesiologica Taiwanica, vol. 53, 2015, pp. 16-22.

* cited by examiner

*Primary Examiner* — Marcela M Cordero Garcia
(74) *Attorney, Agent, or Firm* — Amster, Rothstein & Ebenstein LLP

(57) ABSTRACT

A method of treating a disease or reducing the development of a symptom of a disease in a subject by administering to the subject an amount of tetranectin protein or a tetranectin peptide agonist effective to treat or reduce development of the disease or disease symptom.

11 Claims, 13 Drawing Sheets

Specification includes a Sequence Listing.

```
                        SEQUENCE LISTING

<160> NUMBER OF SEQ ID NOS: 18

<210> SEQ ID NO 1
<211> LENGTH: 9
<212> TYPE: PRT
<213> ORGANISM: Homo sapiens

<400> SEQUENCE: 1

Leu Gln Thr Val Cys Leu Lys Gly Thr
1               5

<210> SEQ ID NO 2
<211> LENGTH: 16
<212> TYPE: PRT
<213> ORGANISM: Homo sapiens

<400> SEQUENCE: 2

Lys Val His Met Lys Cys Phe Leu Ala Phe Thr Gln Thr Lys Thr Phe
1               5                   10                  15

<210> SEQ ID NO 3
<211> LENGTH: 12
<212> TYPE: PRT
<213> ORGANISM: Homo sapiens

<400> SEQUENCE: 3

His Glu Ala Ser Glu Asp Cys Ile Ser Arg Gly Gly
1               5                   10

<210> SEQ ID NO 4
<211> LENGTH: 10
<212> TYPE: PRT
<213> ORGANISM: Homo sapiens

<400> SEQUENCE: 4

Gly Gly Thr Leu Gly Thr Pro Gln Thr Gly
1               5                   10
```

```
<210> SEQ ID NO 5
<211> LENGTH: 24
<212> TYPE: PRT
<213> ORGANISM: Homo sapiens

<400> SEQUENCE: 5

Thr Pro Gln Thr Gly Ser Glu Asn Asp Ala Leu Tyr Glu Tyr Leu Arg
1               5                   10                  15

Gln Ser Val Gly Asn Glu Ala Glu
            20

<210> SEQ ID NO 6
<211> LENGTH: 18
<212> TYPE: PRT
<213> ORGANISM: Homo sapiens

<400> SEQUENCE: 6

Gly Asn Glu Ala Glu Ile Trp Leu Gly Leu Asn Asp Met Ala Ala Glu
1               5                   10                  15

Gly Thr

<210> SEQ ID NO 7
<211> LENGTH: 24
<212> TYPE: PRT
<213> ORGANISM: Homo sapiens

<400> SEQUENCE: 7

Gly Thr Trp Val Asp Met Thr Gly Ala Arg Ile Ala Tyr Lys Asn Trp
1               5                   10                  15

Glu Thr Glu Ile Thr Ala Gln Pro
            20

<210> SEQ ID NO 8
<211> LENGTH: 13
<212> TYPE: PRT
<213> ORGANISM: Homo sapiens

<400> SEQUENCE: 8

Ile Thr Ala Gln Pro Asp Gly Gly Lys Thr Glu Asn Cys
1               5                   10

<210> SEQ ID NO 9
<211> LENGTH: 17
<212> TYPE: PRT
<213> ORGANISM: Homo sapiens

<400> SEQUENCE: 9

Asn Cys Ala Val Leu Ser Gly Ala Ala Asn Gly Lys Trp Phe Asp Lys
1               5                   10                  15

Arg

<210> SEQ ID NO 10
<211> LENGTH: 24
<212> TYPE: PRT
<213> ORGANISM: Homo sapiens

<400> SEQUENCE: 10

Ala Ala Asn Gly Lys Trp Phe Asp Lys Arg Cys Arg Asp Gln Leu Pro
1               5                   10                  15

Tyr Ile Cys Gln Phe Gly Ile Val
            20
```

```
<210> SEQ ID NO 11
<211> LENGTH: 28
<212> TYPE: PRT
<213> ORGANISM: Homo sapiens

<400> SEQUENCE: 11

Gln Pro Asp Gly Gly Lys Thr Glu Asn Cys Ala Val Leu Ser Gly Ala
1               5                   10                  15

Ala Asn Gly Lys Trp Phe Asp Lys Arg Cys Arg Asp
            20                  25

<210> SEQ ID NO 12
<211> LENGTH: 137
<212> TYPE: PRT
<213> ORGANISM: Homo sapiens

<400> SEQUENCE: 12

Ala Leu Gln Thr Val Cys Leu Lys Gly Thr Lys Val His Met Lys Cys
1               5                   10                  15

Phe Leu Ala Phe Thr Gln Thr Lys Thr Phe His Glu Ala Ser Glu Asp
                20                  25                  30

Cys Ile Ser Arg Gly Gly Thr Leu Gly Thr Pro Gln Thr Gly Ser Glu
            35                  40                  45

Asn Asp Ala Leu Tyr Glu Tyr Leu Arg Gln Ser Val Gly Asn Glu Ala
        50                  55                  60

Glu Ile Trp Leu Gly Leu Asn Asp Met Ala Ala Glu Gly Thr Trp Val
65                  70                  75                  80

Asp Met Thr Gly Ala Arg Ile Ala Tyr Lys Asn Trp Glu Thr Glu Ile
                85                  90                  95

Thr Ala Gln Pro Asp Gly Gly Lys Thr Glu Asn Cys Ala Val Leu Ser
            100                 105                 110

Gly Ala Ala Asn Gly Lys Trp Phe Asp Lys Arg Cys Arg Asp Gln Leu
        115                 120                 125

Pro Tyr Ile Cys Gln Phe Gly Ile Val
    130                 135

<210> SEQ ID NO 13
<211> LENGTH: 16
<212> TYPE: PRT
<213> ORGANISM: Artificial Sequence
<220> FEATURE:
<223> OTHER INFORMATION: artificial sequence based on human sequence
<220> FEATURE:
<221> NAME/KEY: MISC_FEATURE
<222> LOCATION: (5)..(5)
<223> OTHER INFORMATION: x=norleucine

<400> SEQUENCE: 13

Thr Lys Val His Xaa Lys Ser Phe Leu Ala Phe Thr Gln Thr Lys Thr
1               5                   10                  15

<210> SEQ ID NO 14
<211> LENGTH: 181
<212> TYPE: PRT
<213> ORGANISM: Homo sapiens

<400> SEQUENCE: 14

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
                20                  25                  30
```

```
Leu Ala Gln Glu Val Ala Leu Leu Lys Glu Gln Ala Leu Gln Thr
         35                  40                  45

Val Cys Leu Lys Gly Thr Lys Val His Met Lys Cys Phe Leu Ala Phe
 50                  55                  60

Thr Gln Thr Lys Thr Phe His Glu Ala Ser Glu Asp Cys Ile Ser Arg
65                  70                  75                  80

Gly Gly Thr Leu Gly Thr Pro Gln Thr Gly Ser Glu Asn Asp Ala Leu
                 85                  90                  95

Tyr Glu Tyr Leu Arg Gln Ser Val Gly Asn Glu Ala Glu Ile Trp Leu
                100                 105                 110

Gly Leu Asn Asp Met Ala Ala Glu Gly Thr Trp Val Asp Met Thr Gly
             115                 120                 125

Ala Arg Ile Ala Tyr Lys Asn Trp Glu Thr Glu Ile Thr Ala Gln Pro
    130                 135                 140

Asp Gly Gly Lys Thr Glu Asn Cys Ala Val Leu Ser Gly Ala Ala Asn
145                 150                 155                 160

Gly Lys Trp Phe Asp Lys Arg Cys Arg Asp Gln Leu Pro Tyr Ile Cys
                165                 170                 175

Gln Phe Gly Ile Val
            180

<210> SEQ ID NO 15
<211> LENGTH: 181
<212> TYPE: PRT
<213> ORGANISM: Mus musculus

<400> SEQUENCE: 15

Glu Ser Pro Thr Pro Lys Ala Lys Lys Ala Asn Ala Lys Lys Asp
1               5                  10                  15

Leu Val Ser Ser Lys Met Phe Glu Glu Leu Lys Asn Arg Met Asp Val
             20                  25                  30

Leu Ala Gln Glu Val Ala Leu Leu Lys Glu Lys Gln Ala Leu Gln Thr
         35                  40                  45

Val Cys Leu Lys Gly Thr Lys Val Asn Leu Lys Cys Leu Leu Ala Phe
 50                  55                  60

Thr Gln Pro Lys Thr Phe His Glu Ala Ser Glu Asp Cys Ile Ser Gln
65                  70                  75                  80

Gly Gly Thr Leu Gly Thr Pro Gln Ser Glu Leu Glu Asn Glu Ala Leu
                 85                  90                  95

Phe Glu Tyr Ala Arg His Ser Val Gly Asn Asp Ala Asn Ile Trp Leu
                100                 105                 110

Gly Leu Asn Asp Met Ala Ala Glu Gly Ala Trp Val Asp Met Thr Gly
             115                 120                 125

Gly Leu Leu Ala Tyr Lys Asn Trp Glu Thr Glu Ile Thr Thr Gln Pro
    130                 135                 140

Asp Gly Gly Lys Ala Glu Asn Cys Ala Ala Leu Ser Gly Ala Ala Asn
145                 150                 155                 160

Gly Lys Trp Phe Asp Lys Arg Cys Arg Asp Gln Leu Pro Tyr Ile Cys
                165                 170                 175

Gln Phe Ala Ile Val
            180

<210> SEQ ID NO 16
<211> LENGTH: 12
<212> TYPE: PRT
<213> ORGANISM: Homo sapiens
```

```
<400> SEQUENCE: 16

Leu Asp Thr Leu Ala Gln Glu Val Ala Leu Leu Lys
1               5                   10

<210> SEQ ID NO 17
<211> LENGTH: 5
<212> TYPE: PRT
<213> ORGANISM: Artificial Sequence
<220> FEATURE:
<223> OTHER INFORMATION: artifical  linker sequence

<400> SEQUENCE: 17

Gly Gly Gly Gly Ser
1               5

<210> SEQ ID NO 18
<211> LENGTH: 5
<212> TYPE: PRT
<213> ORGANISM: Artificial Sequence
<220> FEATURE:
<223> OTHER INFORMATION: Artificial linker sequence

<400> SEQUENCE: 18

Glu Ala Ala Ala Lys
1               5
```

USE OF TETRANECTIN AND PEPTIDE AGONISTS TO TREAT INFLAMMATORY DISEASES

CROSS-REFERENCE TO RELATED APPLICATIONS

This application is a U.S. national stage entry under 35 U.S.C. § 371 of PCT International Patent Application No. PCT/US2018/035821, filed Jun. 4, 2018, which claims the benefit of U.S. Provisional Application No. 62/514,085, filed Jun. 2, 2017, the contents of which are hereby incorporated by reference.

GOVERNMENT SUPPORT CLAUSE

This invention was made with government support under grant numbers GM063075 and AT005076 awarded by the National Institutes of Health. The government has certain rights in the invention.

BACKGROUND OF THE INVENTION

Throughout this application various publications are referred to. The disclosures of these publications, and of all patents, patent application publications and books referred to herein, are hereby incorporated by reference in their entirety into the subject application to more fully describe the art to which the subject invention pertains.

Despite recent advances in the antibiotic therapy and intensive care, bacterial infections and sepsis remain widespread problems in critically ill patients. Sepsis is a common and difficult to treat pathology with a high mortality rate. There are more than 1 million cases of sepsis each year, according to the Centers for Disease Control and Prevention (CDC) and more than 258,000 resultant fatalities in the U.S. The pathogenesis of sepsis remains obscure, but is partly attributable to the dys-regulated systemic inflammation and coagulation/fibrinolysis propagated by the innate immune cells (IMCs, such as macrophages and monocytes) in response to microbial infections [1-3]. IMCs are equipped with various pattern recognition receptors [PRRs, such as the Toll-like receptors (TLRs), TLR2, TLR4, and TLR9] to recognize various pathogen-associated molecular patterns [PAMPs, e.g., bacterial endotoxins (lipopolysaccharide, LPS) and CpG-DNAs] [4-7]. Upon LPS binding to the high-affinity transmembrane receptor, TLR4 [8], IMCs immediately release "early" cytokines such as TNF [9], IL-10 [10] and IFN-γ [11]. If dys-regulated, the excessive production of these early cytokines adversely contributes to the pathogenesis of lethal systemic inflammation (LSI). However, the therapeutic windows for these early cytokines are relatively narrower, prompting the search for other "late" mediators that may offer better therapeutic opportunities.

The present invention addresses the need for improved methods and new compositions for treating sepsis.

SUMMARY OF THE INVENTION

A method of treating endotoxemia or sepsis in a subject comprising administering to the subject having endotoxemia or sepsis an amount of a tetranectin protein or a tetranectin peptide agonist effective to treat endotoxemia or sepsis in a subject.

A method of reducing the likelihood of death from endotoxemia or sepsis in a subject having endotoxemia or sepsis, the method comprising administering to the subject an amount of tetranectin protein or a tetranectin peptide agonist effective to treat endotoxemia or sepsis in a subject.

A method of reducing the likelihood of endotoxemia or sepsis developing in a subject comprising administering to the subject an amount of tetranectin protein or a tetranectin peptide agonist effective to reduce the likelihood of endotoxemia or sepsis developing in a subject.

A method of reducing development of sepsis-associated coagulation in a subject comprising administering to the subject an amount of tetranectin protein or a tetranectin peptide agonist effective to reduce the development of sepsis-associated coagulation in a subject.

A method of reducing development of fibrinolysis in a subject comprising administering to the subject an amount of tetranectin protein or a tetranectin peptide agonist effective to reduce the development of fibrinolysis in a subject.

A method of eliciting production of a neutrophil-attracting chemokine in a subject comprising administering to the subject an amount of a tetranectin protein or a tetranectin peptide agonist effective to elicit production of a neutrophil-attracting chemokine.

A method of treating an inflammatory disease in a subject comprising administering to the subject an amount of a tetranectin protein or a tetranectin peptide agonist effective to treat an inflammatory disease in a subject.

DETAILED DESCRIPTION OF THE INVENTION

Figure 1:
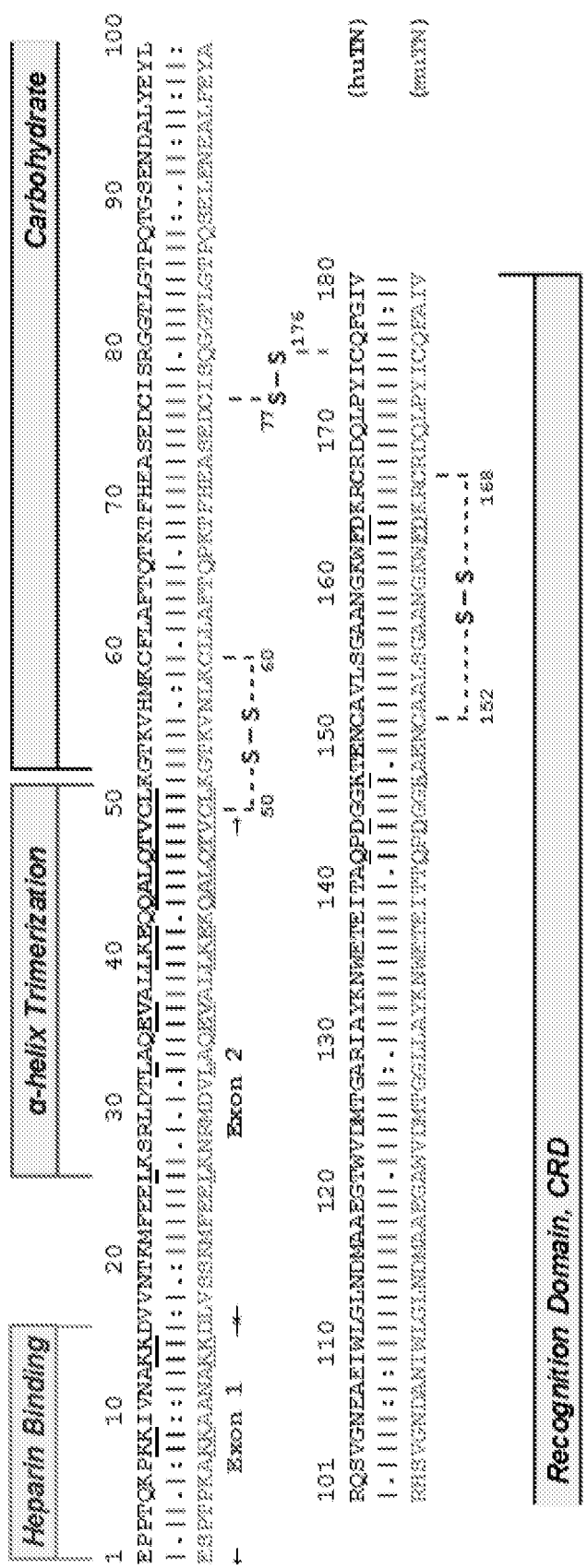
FIG. 1: Functional domains of human (SEQ ID NO:14) and murine (SEQ ID NO:15) tetranectin (TN). Three exons [1: 1-16; 2: 17-49, and 3: 50-181], three predicted disulfide bonds (50-60, 77-176, and 152-168), and some key residues for each functional domains are indicated.

A method of treating endotoxemia or sepsis in a subject comprising administering to the subject having endotoxemia or sepsis an amount of a tetranectin protein or a tetranectin peptide agonist effective to treat endotoxemia or sepsis in a subject.

A method of reducing the likelihood of death from endotoxemia or sepsis in a subject having endotoxemia or sepsis, the method comprising administering to the subject an amount of tetranectin protein or a tetranectin peptide agonist effective to treat endotoxemia or sepsis in a subject.

A method of reducing the likelihood of endotoxemia or sepsis developing in a subject comprising administering to the subject an amount of tetranectin protein or a tetranectin peptide agonist effective to reduce the likelihood of endotoxemia or sepsis developing in a subject.

A method of reducing development of sepsis-associated coagulation in a subject comprising administering to the subject an amount of tetranectin protein or a tetranectin peptide agonist effective to reduce the development of sepsis-associated coagulation in a subject.

A method of reducing development of fibrinolysis in a subject comprising administering to the subject an amount of tetranectin protein or a tetranectin peptide agonist effective to reduce the development of fibrinolysis in a subject.

In an embodiment, the subject is a human subject.

In an embodiment, the subject is 60 years or older, or is immunocompromised.

In an embodiment, the amount of tetranectin protein is administered and the tetranectin protein is a recombinantly produced tetranectin protein.

In an embodiment, the amount of tetranectin protein is administered and the tetranectin protein has the sequence of a human tetranectin protein but is not isolated from, or produced in, a human.

In an embodiment, the amount of tetranectin peptide agonist is administered.

In an embodiment, the tetranectin peptide agonist comprises a sequence of a plasminogen-binding region of a tetranectin protein.

In an embodiment, the amount of tetranectin peptide agonist comprises a N-terminal deletion of tetranectin protein.

In an embodiment, the tetranectin peptide agonist comprises one of SEQ ID NOS:1-13 with 0, 1, 2 or 3 amino acids, independently, at either C terminal, or N terminal, or both terminals thereof. In an embodiment, the tetranectin peptide agonist comprises SEQ ID NO:11. In an embodiment, the tetranectin peptide agonist consists of SEQ ID NO:11 with 0, 1, 2 or 3 amino acids amino acids, independently, at either C terminal, or N terminal, or both terminals thereof. In an embodiment, the tetranectin peptide agonist comprises SEQ ID NO:12. In an embodiment, the tetranectin peptide agonist consists of SEQ ID NO:12 with 0, 1, 2 or 3 amino acids, independently, at either C terminal, or N terminal, or both terminals thereof. In an embodiment, the tetranectin peptide agonist comprises SEQ ID NO:13. In an embodiment, the tetranectin peptide agonist consists of SEQ ID NO:13 with 0, 1, 2 or 3 amino acids, independently, at either C terminal, or N terminal, or both terminals thereof. In an embodiment, the tetranectin peptide agonist comprises SEQ ID NO:2. In an embodiment, the tetranectin peptide agonist consists of SEQ ID NO:2 with 0, 1, 2 or 3 amino acids, independently, at either C terminal, or N terminal, or both terminals thereof. In embodiments, the tetranectin peptide agonist does not comprise a full length naturally-occurring tetranectin sequence. In embodiments, the tetranectin peptide agonist does not comprise SEQ ID NO:15. In embodiments, the tetranectin peptide agonist does not comprise SEQ ID NO:16.

In an embodiment of the methods, the tetranectin protein or tetranectin peptide agonist is fused to a molecule that increases plasma-half life of the peptide. In an embodiment of the methods, the tetranectin protein or tetranectin peptide agonist is fused to an XTEN molecule, a PEG molecule, or an albumin molecule. In an embodiment of the methods, the tetranectin protein or tetranectin peptide agonist is not fused to another peptide or protein molecule.

In an embodiment, the tetranectin protein or tetranectin peptide agonist is administered as a fusion protein. In an embodiment, the administered tetranectin protein or tetranectin peptide agonist is not a fusion protein. In one embodiment, when administered as a fusion protein, the peptide is fused to a portion of an immunoglobulin, e.g. a portion of an IgG or an IgM. In an embodiment, it as a portion of an IgG. The IgG portion of the fusion protein can be, e.g., any of an IgG1, IgG2, IgG2a, IgG2b, IgG3 or IgG4 or a portion thereof. In an embodiment, the portion is an Fc region. In an embodiment the fusion protein comprises a sequence identical to an Fc portion of a human IgG1, human IgG2, human IgG2a, human IgG2b, human IgG3 or human IgG4. In an embodiment the fusion protein comprises a sequence identical to an Fc portion of a human IgG1. The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, by recombinantly engineering the nucleic acid encoding the fusion protein. In an embodiment, the peptide is linked to the Fc domain through a linker. In an embodiment, it is linked via a peptide linker which permits flexibility. In an embodiment, the linker is rigid. In an embodiment the linker is cleavable. Non-limiting examples of flexible linkers within the scope of the invention are $G_n$, and GGGGS (SEQ ID NO:17), and $(GGGGS)_n$ (SEQ ID NO:17) where n=2, 3, 4 or 5. Non-limiting examples of rigid linkers within the scope of the invention are $(EAAAK)_n$, (SEQ ID NO:18), $(XP)_n$. Non-limiting examples of cleavable linkers within the scope of the invention include disulfide links and protease cleavable linkers. In a preferred embodiment, the linker is a peptide linker. In an embodiment, the Fc domain has the same sequence or 95% or greater sequence similarity with a human IgG1 Fc domain. In an embodiment, the Fc domain has the same sequence or 95% or greater sequence similarity with a human IgG2 Fc domain. In an embodiment, the Fc domain has the same sequence or 95% or greater sequence similarity with a human IgG3 Fc domain. In an embodiment, the Fc domain has the same sequence or 95% or greater sequence similarity with a human IgG4 Fc domain. In an embodiment, the Fc domain is not mutated. In an embodiment, the Fc domain is mutated at the CH2-CH3 domain interface to increase the affinity of IgG for FcRn at acidic but not neutral pH (Dall'Acqua et al, 2006; Yeung et al, 2009). In an embodiment, the fusion protein described herein is recombinantly produced. In an embodiment, the fusion protein is produced in a eukaryotic expression system. In an embodiment, the fusion protein produced in the eukaryotic expression system comprises glycosylation at a residue on the Fc portion corresponding to Asn297. In an embodiment, the fusion protein is a homodimer. In an embodiment, the fusion protein is monomeric. In an embodiment, the fusion protein is polymeric.

In an embodiment, the method further comprises one or more additional administration(s) of an amount of tetranectin protein or of tetranectin peptide agonist subsequent to the first administration.

A method of eliciting production of a neutrophil-attracting chemokine in a subject comprising administering to the subject an amount of a tetranectin protein or a tetranectin peptide agonist effective to elicit production of a neutrophil-attracting chemokine.

In an embodiment, the neutrophil-attracting chemokine is CXCL1/GRO-α/KC or CXCL5/ENA-78.

A method of treating an inflammatory disease in a subject comprising administering to the subject an amount of a tetranectin protein or a tetranectin peptide agonist effective to treat an inflammatory disease in a subject.

In an embodiment, the amount of tetranectin protein is administered and the tetranectin protein is a recombinantly produced tetranectin peptide.

In an embodiment, the amount of tetranectin protein is administered and the tetranectin protein has the sequence of a human tetranectin protein but is not isolated from, or produced in, a human.

In an embodiment, the amount of tetranectin peptide agonist is administered.

In an embodiment, the tetranectin peptide agonist comprises a sequence of a plasminogen-binding region of a tetranectin protein.

In an embodiment, the amount of tetranectin peptide agonist comprises a N-terminal deletion of tetranectin protein.

In an embodiment of the methods, the composition is administered intravenously. Alternative routes of administration embodied herein are auricular, buccal, conjunctival, cutaneous, subcutaneous, endocervical, endosinusial, endotracheal, enteral, epidural, via hemodialysis, interstitial, intrabdominal, intraamniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronary, intradermal, intradiscal, intraductal, intraepidermal, intraesophagus, intragastric, intravaginal, intragingival, intraileal, intraluminal, intralesional, intralymphatic, intramedullary, intrameningeal, intramuscular, intraocular, intraovarian, intraepicardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intraventricular, intravesical, intravitreal, laryngeal, nasal, nasogastric, ophthalmic, oral, oropharyngeal, parenteral, percutaneous, periarticular, peridural, rectal, inhalationally, retrobulbar, subarachnoid, subconjuctival, sublingual, submucosal, topically, transdermal, transmucosal, transplacental, transtracheal, ureteral, urethereal, and vaginal.

As used herein, "treating" sepsis means that one or more symptoms of the disease, such as inflammation, cytokine release, organ dysfunction, or other parameters by which the disease is characterized, are reduced, ameliorated, prevented, or placed in a state of retreat.

In an embodiment of the composition, the peptide consists of L-amino acids.

In an embodiment of the composition, the peptide comprises L-amino acids and D-amino acids.

In an embodiment of the composition, the peptide consists of D-amino acids.

In an embodiment of the composition, the composition comprises a pharmaceutically acceptable carrier.

"Carrier": The term "carrier" is used in accordance with its art-understood meaning, to refer to a material that is included in a pharmaceutical composition but does not abrogate the biological activity of pharmaceutically active agent(s) that are also included within the composition. Typically, carriers have very low toxicity to the animal to which such compositions are to be administered. In some embodiments, carriers are inert. In some embodiments, carriers are affirmatively beneficial. In some embodiments, the term "carrier" when used in the pharmaceutical context (e.g., pharmaceutically acceptable carrier) means that an agent is present in a composition but does not abrogate the biological activity of another agent(s) present in a composition, for example the peptide of the composition.

"Pharmaceutically acceptable": The term "pharmaceutically acceptable" as used herein applied to carriers refers to those carriers which are, within the scope of medical judgment, suitable for use in contact with the tissues of humans and lower animals without undue toxicity, irritation, allergic response, and the like, commensurate with a reasonable benefit/risk ratio, and effective for their intended use.

The compositions of the inventions can comprise one or more additional components which facilitate use of the composition in treating sepsis or liver damage, or which enhance storage properties of the composition. For example, pH adjusting agent, and preservative(s).

"pH adjusting agent": As used herein, the term "pH adjusting agent" as used herein is an agent that imparts suitable pH characteristics to compositions provided herein, (e.g., a substantially neutral pH, e.g. pH 7.35), the pH of which depends on the specific utilization of the composition. Suitable pH adjusting agents include, for example, but are not limited to, one or more adipic acids, buffers, citric acids, calcium hydroxides, glycines, magnesium aluminometasilicates, or combinations thereof.

"Preservative": As used herein, the term "preservative" has its art-understood meaning and refers to an agent that protects against undesirable chemical modifications of one or more components in a composition (e.g., protection against an undesirable chemical modification of an active ingredient). Suitable preservatives for use in the compositions of the present invention include, but are not limited to, one or more alkanols, disodium EDTA, EDTA salts, EDTA fatty acid conjugates, isothioazolinone, parabens such as methylparaben and propylparaben, polypropylene glycols, sorbates, urea derivatives such as diazolindinyl urea, or combinations thereof.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

To search for endogenous HMGB1 regulators, the dynamic changes of circulating HMGB1 and other proteins were systematically monitored in normal healthy subjects versus septic patients, and a negative correlation was found between levels of circulating HMGB1 and tetranectin, a plasminogen-binding protein implicated in binding plasminogen to activate the plasmin-dependent fibrinolysis.

Data was then obtained showing that the highly purified recombinant TN and peptide agonist (e.g., P11 and P12, Table 1) dose-dependently attenuated the LPS/SAA-induced HMGB1 release, but specifically stimulated the release of several neutrophil-attracting chemokines (CXCL1 and CXCL5) by primary human monocytes. In animal models of lethal endotoxemia and sepsis (induced by cecal ligation and puncture, CLP), circulating TN levels were time-dependently decreased; whereas the supplementation with highly purified recombinant TN and peptide agonist (e.g., P11 and P12, Table 1) conferred a significant protection.

Example 1

It was discovered that the high mobility group box-1 (HMGB1) protein [12] is actively secreted by IMCs in response to the stimulation with various PAMPs (e.g., LPS or CpG-DNA) [12,13] or host proinflammatory cytokines (e.g., IFN-γ, IFN-β, CIRP, and SAA) [14-17]. Once released, extracellular HMGB1 functions as an alarmin signal to alert, recruit and activate IMCs [18-22], thereby sustaining a rigorous and potentially injurious LSI. In animal models of lethal endotoxemia and sepsis (induced by cecal ligation and puncture, CLP), circulating HMGB1 levels plateau within 24-36 h [12,23], distinguishing it from TNF and other early cytokines [24]. Moreover, HMGB1-neutralizing antibodies [12,23,25] confer protection against lethal endotoxemia and sepsis, even when the first dose was given 24 h after CLP, establishing HMGB1 as a "late" mediator of sepsis with a relative wider therapeutic window [24,26-28].

Recently, HMGB1 has also been implicated in the pathogenesis of the dys-regulated coagulopathy [29]. In vitro, HMGB1 stimulated tissue factor (TF) expression [30], and activated platelet aggregation [31]. In animal models of trauma/hemorrhagic shock [32] and venous thrombosis [33], the platelet-derived HMGB1 has been suggested as a key mediator of the platelet aggregation and thrombosis. Indeed, a combined administration of thrombin and HMGB1 resulted in an excessive fibrin deposition, prolonged plasma clotting, and increased animal mortality [34]. In patients with sepsis, the plasma HMGB1 level positively correlated with the development of DIC, supporting a pathogenic role for HMGB1 in the sepsis-induced coagulopathy [35]. Dys-regulated inflammation is integrally linked to excessive pro-coagulant and impaired fibrinolytic responses [36,37]. During sepsis, for instance, the activation of the fibrinolytic cascade becomes transient because the brisk rise of the t-PA/u-PA activity is quickly overwhelmed by the subsequent increase of the plasminogen activator inhibitor-1 (PAI-1) [38], tilting the hemostatic balance toward coagulation to precipitate the development of the disseminated intravascular coagulation (DIC) [3]. Clinically, therapies targeting the coagulation cascade using anticoagulant agents, such as the activated protein C (APC), has shown limited efficacy with unintended risk of hemorrhagic complications in septic patients [39]. It is thus important to explore other therapies to modulate the dys-regulated inflammatory and/or fibrinolytic responses for the management of sepsis.

Mammals have evolved multiple anti-inflammatory pathways to counter-regulate excessive inflammatory responses. For instance, the central nervous system (CNS) can directly attenuate the LPS-induced cytokine production through efferent vagus nerve signals to tissue-resident T cells [40] and macrophages [41]. This effect is mediated by the vagus nerve neurotransmitter, acetylcholine, via the alpha-7 nicotinic cholinergic receptor (α7 nAChR) [41-43]. Another counter-regulatory mechanism relies on the passive release of a ubiquitous biogenic molecule, spermine [44], which accumulates at the injury sites, where it attenuates the synthesis and secretion of various pro-inflammatory cytokines (e.g. TNF, IL-1, MIP-1) from the activated IMCs [45,46]. Disclosed herein is evidence of tetranectin as a negative regulator of HMGB1 release.

Tetranectin (TN) as a plasminogen-binding protein. In 1986, tetranectin (TN) was first characterized as an oligomeric 181-amino acid (AA) polypeptide bound to the 4th kringle of the human plasminogen (PLMG) [47]. Both human and murine TN genes encode a 202-AA protein, which harbors a 21-AA leader signal sequence, and exhibits an overall 76% sequence identity and 87% sequence similarity (FIG. 1) [48]. The TN mRNA is expressed in multiple organs including the heart, brain, lung, liver, skeletal muscle, kidney and pancreas, with the highest abundance in the lung and skeletal muscle [49,50]. TN protein is detected in many endocrine [51] and epithelial tissues (e.g., the pseudostratified respiratory epithelium), as well as in innate immune cells including lymphocytes, macrophages and granulocytes [52]. More importantly, TN protein is present in the human plasma, ranging from a moderate level (~8 μg/ml) in infants to a high level (10-12 μg/ml) in adults, but starting to decrease in the elderly (>60-yr) [53]. It has been speculated that the circulating TN may partly derive from the lung, because there was no distinct TN immunostaining signal despite highest abundance of TN mRNA in this organ [50]. In addition, a small portion (15%) of the plasma TN may derive from the activated platelet during the coagulation and become partially bound to fibrin (FBN) [54].

Extensive studies have revealed several distinct functional domains respectively responsible for: 1) the TN secretion (i.e., the leader signal sequence); 2) the heparin binding; 3) the trimerization; and 4) the carbohydrate recognition and binding (FIG. 1). For instance, the 21-AA leader signal sequence (not shown in FIG. 1) directs the pro-TN to the endoplasmic reticulum, and is then cleaved prior to extracellular secretion of the mature 181-AA TN (FIG. 1). The heparin-binding site resides in the N-terminus, particularly within the decapeptide segment KPK-KIVNAKK (FIG. 1) (i.e. residues 6 to 15 of SEQ ID NO:14) [55]. The α-helical domain, encoded by the exon 2, serves as the driving force for the trimerization of TN proteins by assembling into a triple coiled-coil element. Finally, the carbohydrate recognition domain (CRD) contains the binding site for the 4th kringle of PLMG, and includes residues of the putative carbohydrate binding site [56], K-148, E-150 and D-165 (FIG. 1), for the calcium-sensitive TN-PLMG interaction (Kd=0.5 μM) [57]. Thus, TN has also been termed as the C-type lectin domain family 3 member B (CLEC3B). In addition to plasminogen, TN also binds to other kringle-containing proteins, such as the apolipoprotein A1 (Apo-A1, Kd=0.013 μM) [58], hepatocyte growth factor (HGF), and tissue-type plasminogen activator (t-PA) [59].

Although the biological function of TN remains poorly understood, enforced TN expression by transfecting nude mice with some TN-expressing PC12 tumor cells resulted in an elevation of the production of bone material, suggesting a role for TN in bone formation [60]. In contrast, the disruption of TN expression precipitated the development of the spinal deformity (characterized by an excessive curvature of the thoracic spine) in ⅓ of aged (>6 months) mice [61], as well as symptoms of motor deficits that resemble Parkinson's diseases (such as limb rigidity) in some 15-20-month-old mice [62]. In addition, the knockout of TN gene markedly impaired would healing [63] predominantly during the early process (such as the soft tissue formation), because the capacity for cartilage and new bone formation was well maintained even under TN-deficient conditions [64]. However, a role for TN in the regulation of HMGB release and lethal systemic inflammation was previously unknown.

Figures 2A, 2B:
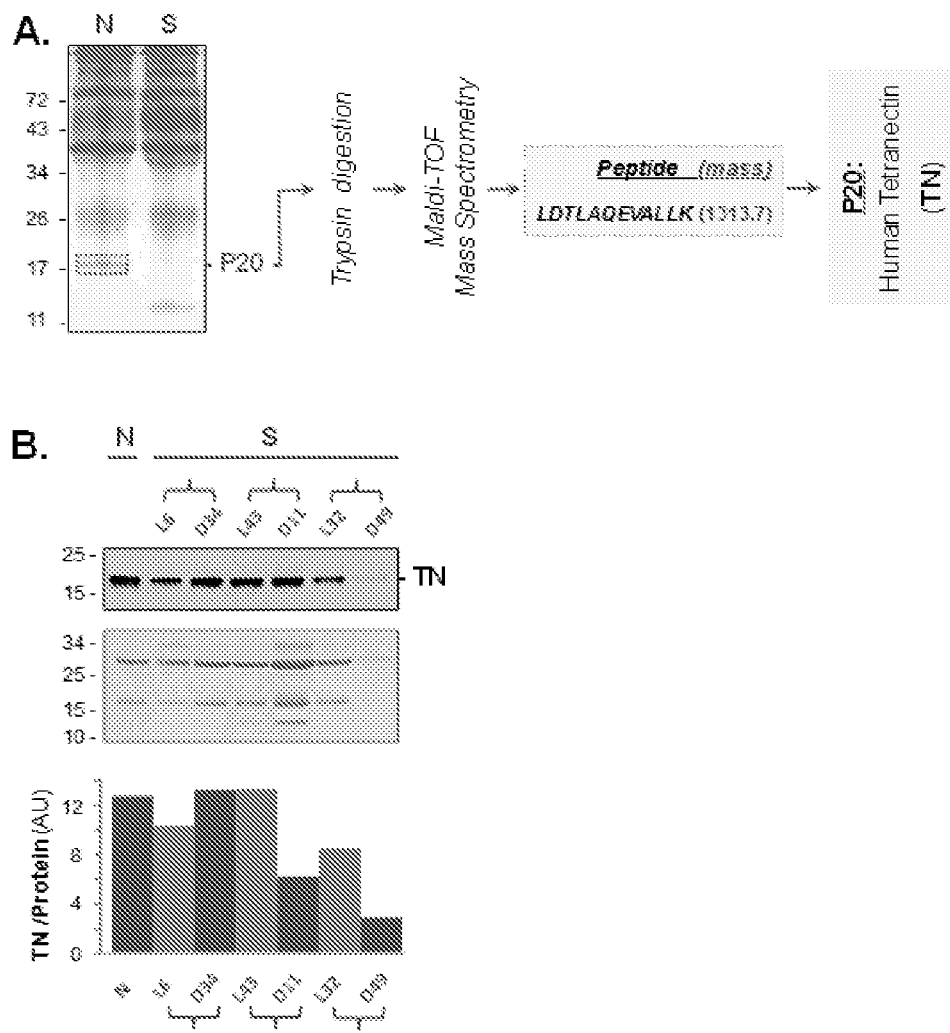
FIG. 2A-2B: Identification of tetranectin (TN) as a serum protein depleted in a septic patient. 2A. Mass spectrometry analysis of a 20 kDa (P20) protein (SEQ ID NO:16), which is abundant in normal healthy individuals (N), but depleted in a septic patient (S). 2B. Western blotting analysis of serum TN in a normal healthy control (N) and three pairs of age- and sex-matched septic survivors (denoted as "L") and non-survivors (denoted as "D").

The discovery of human TN as a negative regulator of HMGB1 release. To search for other endogenous proteins that could also modulate HMGB1 release, the kinetic changes of serum HMGB1 and other proteins were characterized in a group of septic patients that were admitted to the Northwell Health System subsequent to the approval by our institutional IRB ethics committee. The American College of Chest Physicians/Society of Critical Care Medicine Consensus Conference definitions of sepsis and septic shock were used for the diagnosis of these patients [65]. In a subset of septic patients with elevated serum HMGB1 levels (data not shown), the levels of a 20-kDa protein (denoted as the "P20") was obviously reduced as compared to that of normal healthy subjects ("N", FIG. 2A). This protein was identified as the plasminogen-binding protein, tetranectin (TN), by in-gel trypsin digestion and mass spectrometry analysis (FIG. 2B). To verify its identity, serum samples of normal health controls (N) and three pairs of age- and sex-matched septic survivors (L6, L43, L32) versus non-survivors (D34, D11, D49) were immunoblotted with a TN-specific rabbit monoclonal Ab (Cat. No. ab108999, Abcam). It confirmed the depletion of TN in the serum of some septic non-survivors (FIG. 2B), implicating a possible role for TN in the regulation of HMGB1 release during sepsis.

Figures 3A, 3B, 3C:
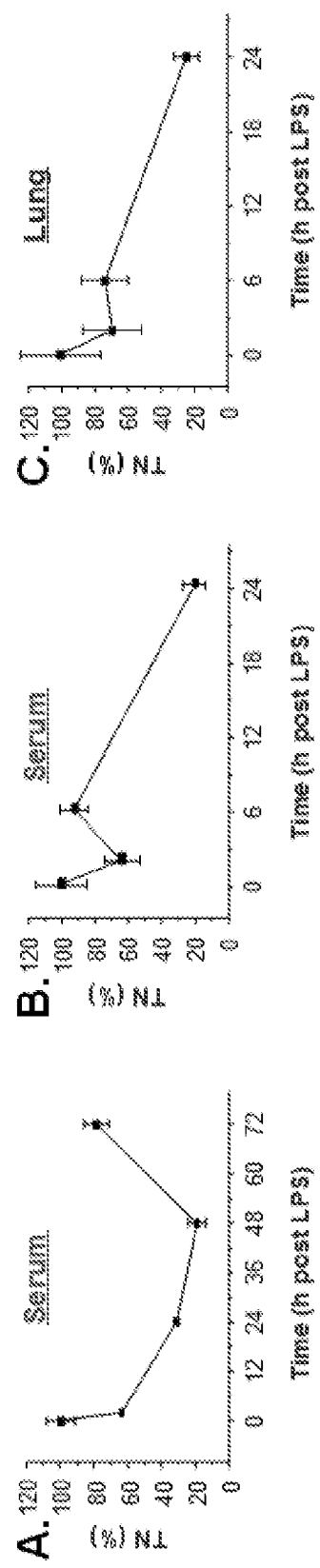
FIG. 3A-3C: TN levels were time-dependently decreased in endotoxemic mice. A, B, Serum TN levels. C, Lung TN levels. The parallel alterations of TN levels in the serum (Panel A, B) and lung (Panel C) support lung as a major source of circulating TN.

Reduction of circulating TN during lethal endotoxemia. To elucidate the possible role of TN in lethal sepsis, its circulating levels were measured in a murine model of lethal endotoxemia. Circulating TN levels were decreased in the endotoxemic mice (FIG. 3A, 3B) in a time-dependent fashion, with a >80% reduction at 24-48 h after the onset of lethal endotoxemia—a time frame when most mice succumbed to death. Afterwards, TN levels started to rebound, returning towards basal levels >72 h post endotoxemia (FIG. 3A), supporting a possibility that the temporal depletion of TN may contribute to the pathogenesis of lethal sepsis. To test the notion that the lung may be a major source of circulating TN [66], the dynamic changes of TN levels was compared in both the serum and lung tissues of the same group of animals. The parallel alteration of TN levels in both the serum (FIG. 3B) and lung tissue (FIG. 3C) of the same set of endotoxemic mice supports the possibility that the lung serves as a major source of circulating TN.

Figures 4A, 4B, 4C:
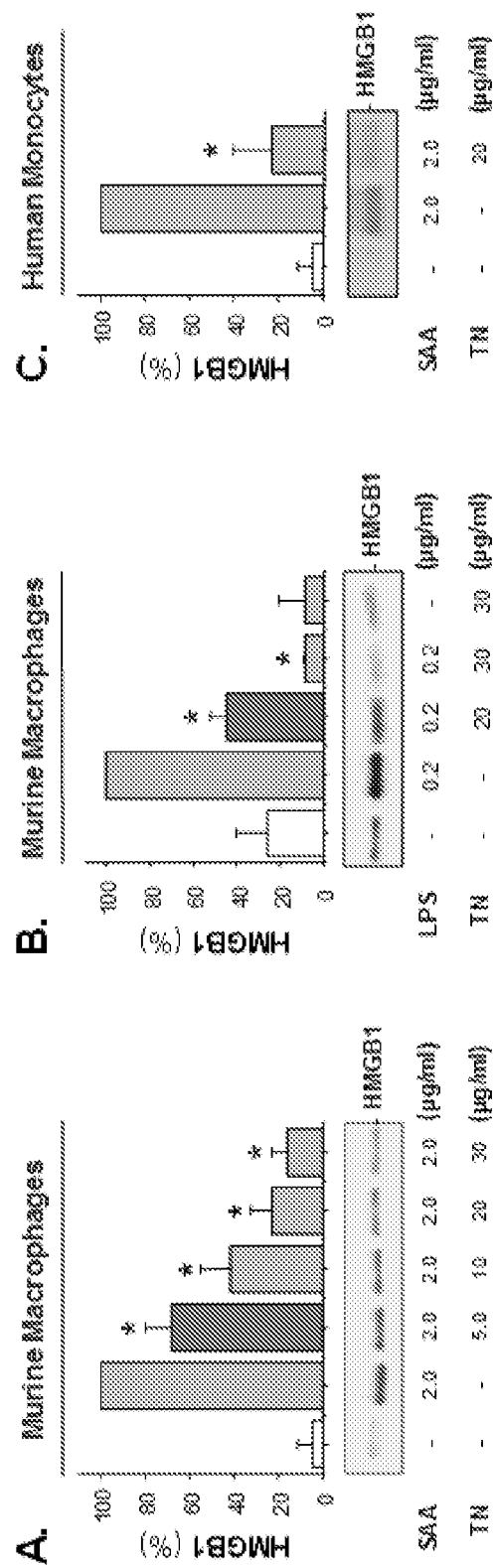
FIG. 4A-4C: TN dose-dependently inhibited the LPS- or SAA-induced HMGB1 release. A, B, Primary murine peritoneal macrophages. C, Primary human peripheral blood mononuclear cells (HuPBMCs). Murine macrophages or human monocytes (HuPBMCs) were cultured in serum-free OPTI-MEM I medium, and stimulated with LPS or SAA for 16 h at the indicated concentrations. The extracellular HMGB1 levels were determined by Western blotting, and expressed as % of maximal stimulation by LPS or SAA alone.

Immune-modulating properties of tetranectin: To explore TN's immune-modulating properties, its effects on the LPS- and SAA-induced HMGB1 release were examined in murine macrophage and human monocyte cultures. Remarkably, the highly purified recombinant human TN protein expressed either in eukaryotes (HEK293 cells) or prokaryotes (E. coli) were all capable of inhibiting the LPS- and SAA-induced HMGB1 release in both murine macrophages (FIG. 4A, 4B) and human monocytes (FIG. 4C). This inhibition was TN-dose-dependent, evident at concentrations as low as 5.0 μg/ml, and became more dramatic (with 50-100% inhibition) at higher doses. Moreover, the inhibition appeared to be specific to HMGB1, because TN did not inhibit the LPS- or SAA-induced release of most other cytokines (e.g., G-CSF, IL-6, IL-12) and chemokines (e.g., KC, LIX, MIP-1α, MIP-2, and RANTES, data not shown).

Figure 5:
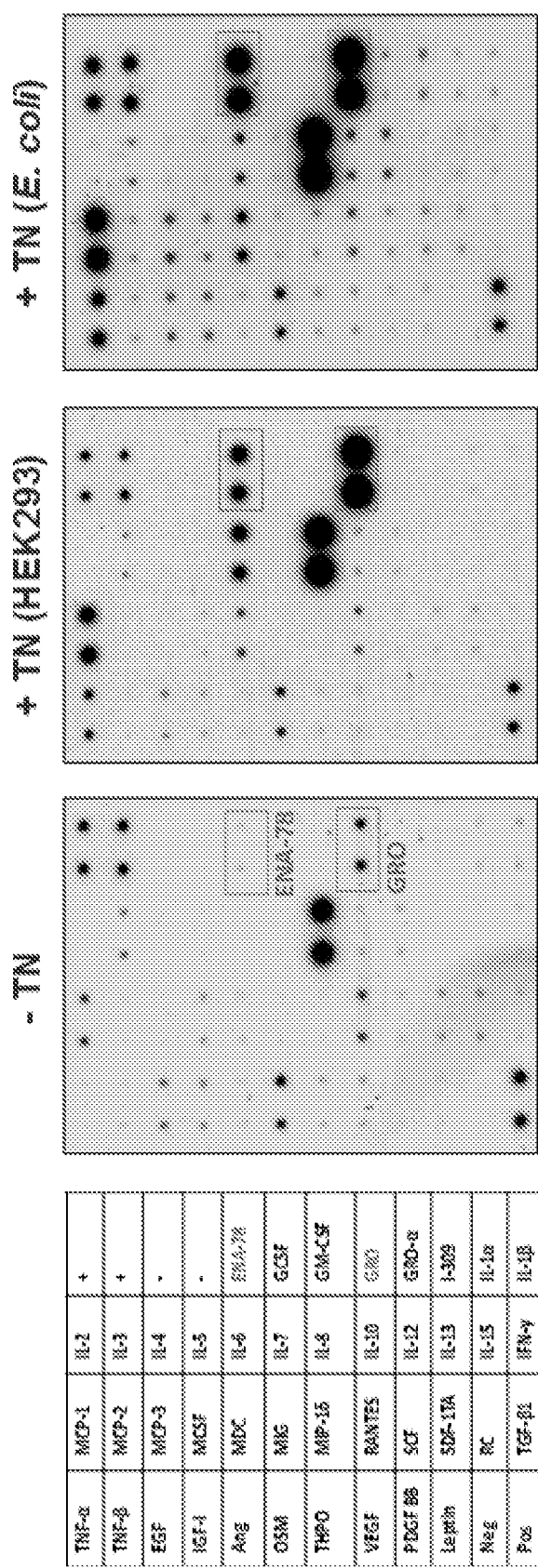
FIG. 5: Recombinant TN specifically induced GRO/CXCL1 and ENA-78/CXCL5 secretion in human peripheral blood mononuclear cells (HuPBMCs). Human blood was purchased from the Long Island Blood Bank, and HuPBMCs were isolated by density gradient centrifugation through Ficoll, and stimulated with recombinant TN (20 µg/ml) expressed in HEK293 or E. coli for 16 h. The extracellular levels of cytokines and chemokines were determined by Cytokine Antibody Arrays.

Intriguingly, TN itself induced the release of several neutrophil-attracting chemokines (CXCL1/GRO-α/KC and CXCL5/ENA-78) from primary human monocytes (FIG. 5). In light of the protective roles of these neutrophil-attracting chemokines, CXCL1/KC [67,68] and CXCL5/ENA-78 [69, 70] in LSI, it is important to determine whether TN could modulate leukocyte infiltration to facilitate potential pathogen elimination during sepsis.

Figures 6A, 6B, 6C:
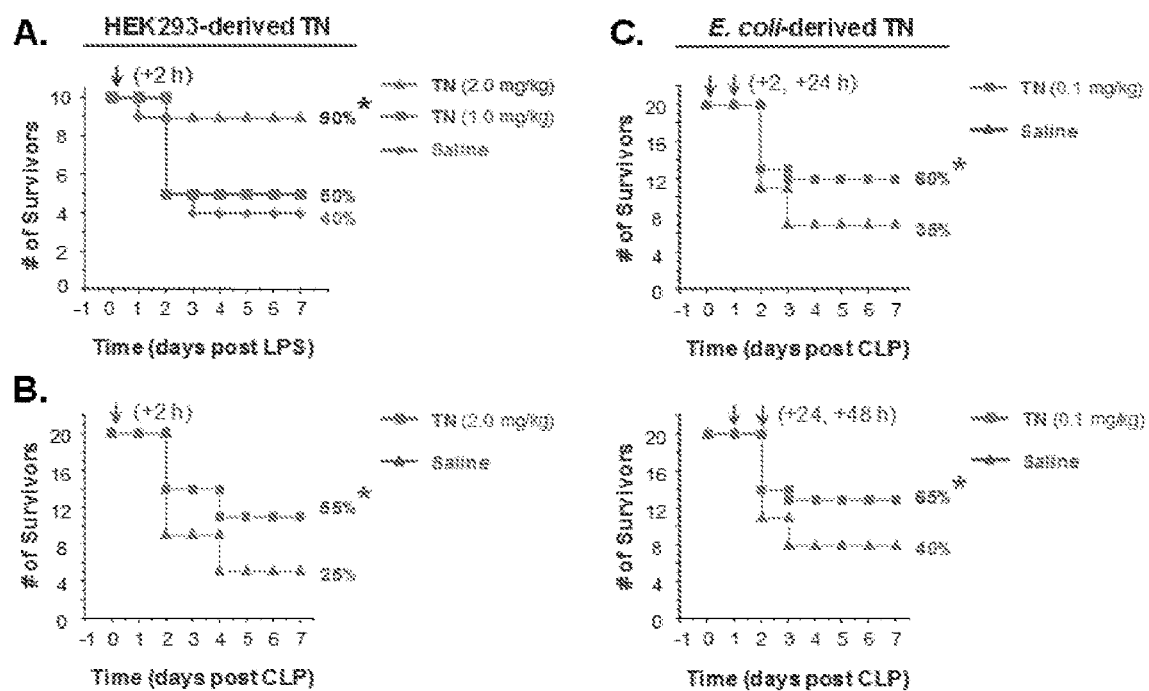
FIG. 6A-6C: Recombinant TN protected mice against lethal endotoxemia and sepsis. Male Balb/C mice were subjected to lethal endotoxemia (LPS, 5 mg/kg, i.p., Panel A) or sepsis by cecal ligation and puncture (CLP, Panel B, C), and recombinant TN produced in HEK293 (Panel A, B) or *E. coli* (Panel C) was given intraperitoneally at indicated dosing regimens. Animal survival rates were monitored for more than two weeks to ensure no later death. Shown in Panel B and C is a summary of two independent experiments with similar results.

Effects of TN or peptide agonist on LSI. Balb/C mice (both male and female, 7-8 weeks, 20-25 g) are subjected to lethal endotoxemia or sepsis as described above, and the recombinant TN is injected (i.p.) at various doses and time points (2, 24, and 48 h) after the onset of endotoxemia or sepsis. Their effects on the outcomes of LSI is assessed by comparing the long-term (two-week) survival rates between the TN-treated groups with saline vehicle-treated controls. By varying the time points (e.g., 2, 12, 24 or 36 h) when the first dose of TN will be given to animals, the therapeutic windows for the TN-based therapy is estimated. As shown in FIG. 6, data obtained shows that the delayed and repetitive administration of TN produced in HEK293 or *E. coli* conferred a significant protection against both lethal endotoxemia (FIG. 6A) and sepsis (FIG. 6B, 6C), supporting a beneficial role of TN in LSI. It will be critical to continue these exciting experiments using other dosing regimens to further validate TN's protective role in LSI.

Figure 7:
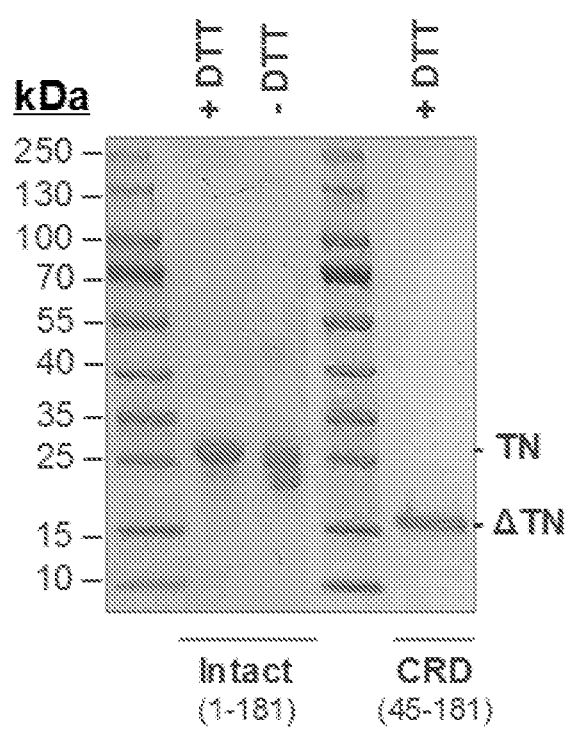
FIG. 7: Expression and purification of recombinant TN and CRD domain. Recombinant TN corresponding to residue 22-202 amino acid (or 1-181 if excluding the 21-residue signal sequence) or the CRD domain corresponding to residue 66-202 (or 45-181) with a C-terminal histidine tag were expressed in *E. coli* BL21 (DE3) pLysS cells, and purified by histidine-affinity and Triton X-114 extraction to remove contaminating endotoxins. Note that recombinant TN migrated on SDS-PAGE gel as a 17 and 24 kDa band in the presence of a reducing agent (DTT), but migrated as 24 kDa band in the absence of DTT, suggesting a possible variation of the redox status of TN protein.
Figure 8:
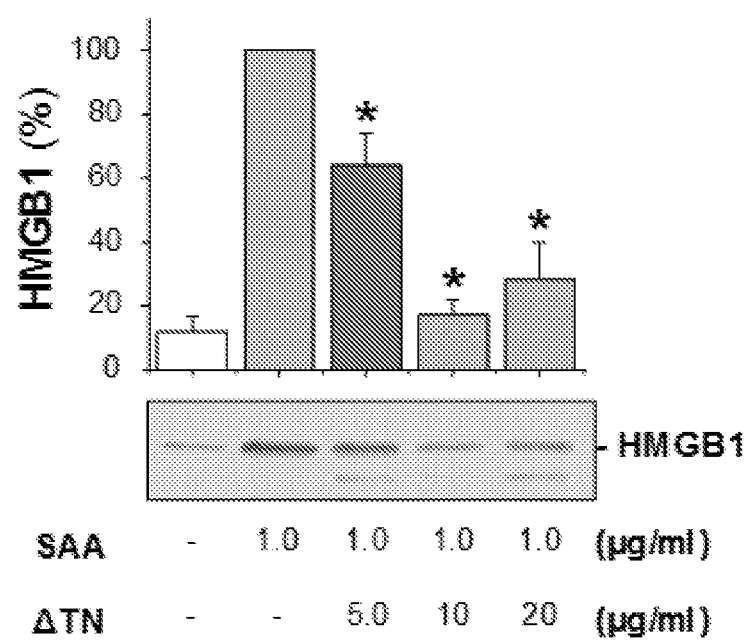
FIG. 8: N-terminal deletion mutant ΔTN dose-dependently inhibited SAA-induced HMGB1 release. Murine macrophage-like RAW264.7 cells were cultured in serum-free OPTI-MEM I medium, and stimulated with SAA in the absence of presence of ΔTN (residue 45-181) for 16 h at the indicated concentrations. The extracellular HMGB1 levels were determined by Western blotting, and expressed as % of stimulation in the presence of SAA alone.
Figure 9:
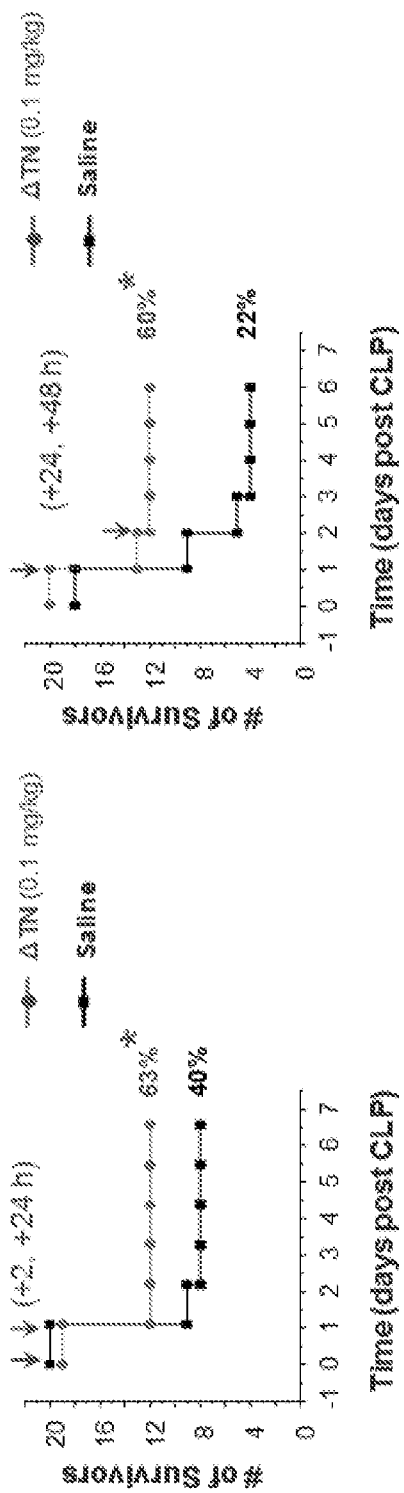
FIG. 9: N-terminal deletion TN mutant protected mice against lethal sepsis. Male Balb/C mice were subjected to lethal sepsis by cecal ligation and puncture (CLP), and recombinant deletion mutant (ΔTN) was given intrapeitoneally at indicated dosing regimens. Animal survival rates were monitored for more than two weeks to ensure no later death. Shown was a summary of two independent experiments with similar results.
Figure 10:
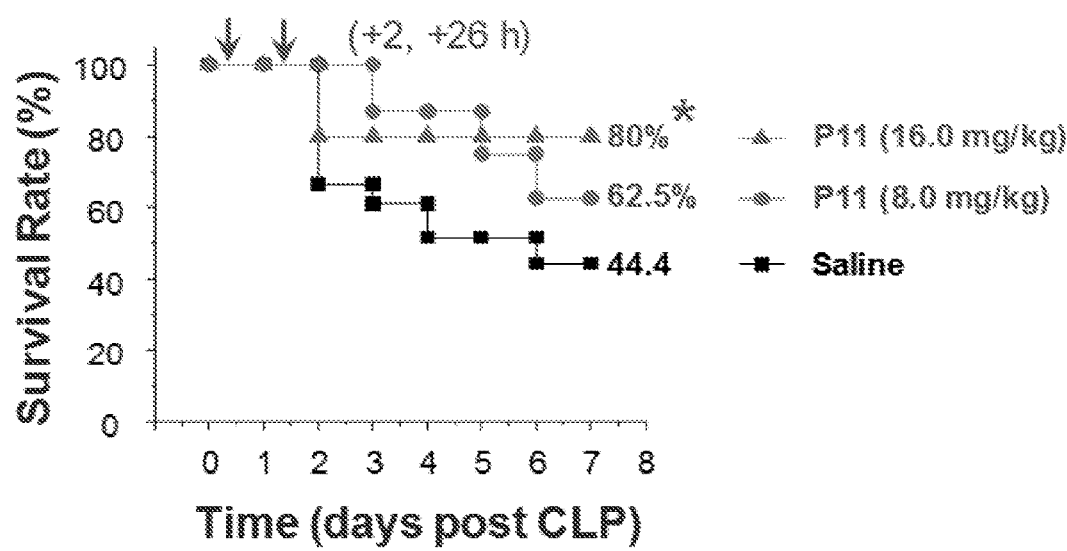
FIG. 10: TN peptide agonist (P11) protected mice against lethal sepsis. Male Balb/C mice were subjected to lethal sepsis by cecal ligation and puncture (CLP), and TN peptide agonist, (P11, QPDGGKTENCAVLSGAANGKWFDKR-CRD) (SEQ ID NO:11) was given intrapeitoneally at indicated dosing regimens. Animal survival rates were monitored for more than two weeks to ensure no later death. Shown was a summary of two independent experiments with N=8-18 animals per group.

To explore the therapeutic potential of the TN-based strategies, the efficacy of TN-specific peptide agonists that would recapitulate the HMGB1-inhibiting capacities is tested using both animal models of lethal endotoxemia and sepsis. A series of peptide agonists have been designed, and chemically synthesized or biologically expressed as recombinant peptide (Table 1, FIG. 7). Peptide agonists will be given to the endotoxemic or septic mice intraperitoneally at various doses and time points after the onset of endotoxemia or sepsis. Their effects on the outcomes of LSI is assessed by comparing the long-term (two-week) survival rates between the peptide agonist groups and the saline vehicle-treated controls. For instance, an N-terminal deletion mutant of TN (FIG. 7 and Table 1) dose-dependently attenuated SAA-induced HMGB1 release (FIG. 8), and conferred significant protection against lethal sepsis even when the first dose of TN peptide was given at 2-24 h post CLP (FIG. 9). Similarly, a synthetic peptide corresponding to the plasminogen-binding region (residue 143-170) conferred a dose-dependent and significant protection against lethal sepsis.

Figure 11:
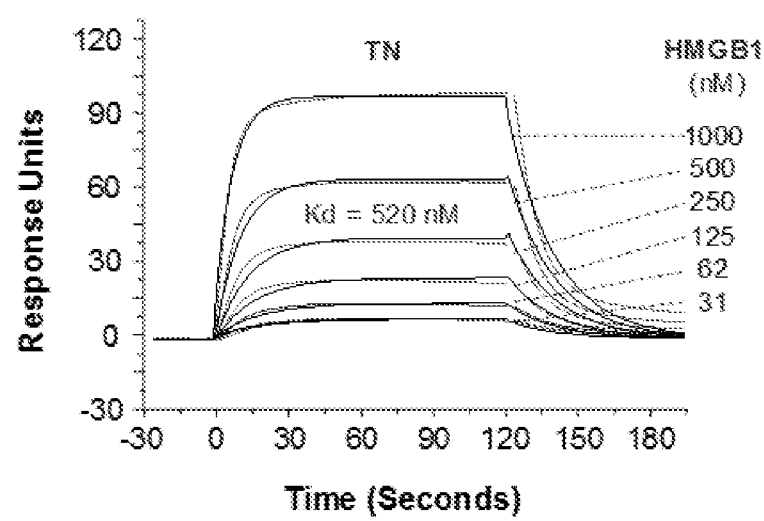
FIG. 11: BIAcore Surface Plasmon Resonance Assay of HMGB1-TN Interaction. Recombinant TN was immobilized on the sensor chip, and HMGB1 was applied as an analyte at different concentrations. The response units were recorded over time, and the binding affinity was estimated as the apparent Kd.

Effects of TN supplementation on the sepsis-induced coagulation. This laboratory has recently discovered that some pharmacological agents (e.g., tanshinones) inhibit HMGB1 release by facilitating its internalization into macrophage cytoplasmic vesicles via the clathrin- and caveolin-dependent endocytosis [71]. Similarly, some endogenous proteins (e.g., haptoglobin) can also capture HMGB1 to enhance its cellular uptake through a CD163 receptor-mediated endocytosis [72]. Thus it is determined whether TN can capture HMGB1 and enhance its internalization into macrophages/monocytes. The TN-HMGB1 interaction is investigated by employing the surface plasmon resonance (SPR) technology as previously described [72, 73]. Briefly, the highly purified recombinant TN or HMGB1 is covalently immobilized on a CM5 chip, and HMGB1 or TN is applied to the chip at various concentrations, before the SPR response will be monitored using a BIAcore system as previously described [72, 73]. Data obtained show that when TN was immobilized on the CM5 chip, HMGB1 exhibited a dose-dependent binding to TN with an estimated Kd of 570 nM (FIG. 11), a binding affinity comparable to that of TN-PLMG interaction (Kd=500 nM) [74].

Figure 12:
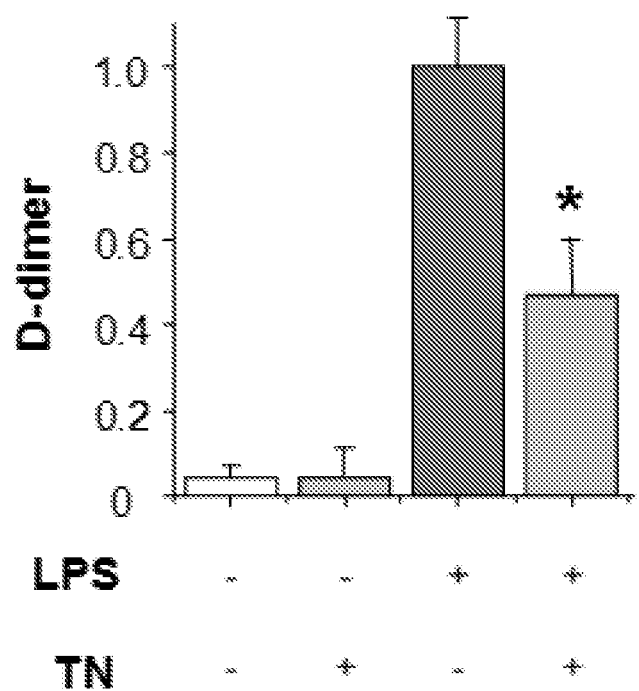
FIG. 12: TN significantly attenuated endotoxin-induced elevation of circulating D-dimer levels. Venous blood was obtained from normal healthy and endotoxemic, Balb/C mice at 24 h post endotoxemia in the absence or presence of recombinant TN. The plasma level of fibrin degradation product (FDP's, e.g., D-dimer) was measured using commercial ELISA kit (Cat. No. EKU03631, Biomatik) as per the manufacturers' instructions. *, $P<0.05$ as compared to the positive control (+LPS alone).

In light of HMGB1's key role in the platelet activation/aggregation and its possible interaction with TN protein, the impact of TN or TN-specific peptide agonists on the pro-fibrinolytic activities is evaluated by measuring the plasma level of fibrin degradation products (FDP's, e.g., D-dimer) using commercial ELISA kits (Cat. No. EKU03631, Biomatik) as per the manufacturers' instructions. A parallel elevation of D-dimer levels is indicative of a possible acceleration of the fibrinolysis cascade by the TN treatment. However, a decrease in the D-dimer concentration is indicative of a reduction of either the plasmin-mediated fibrinolysis or the thrombin-mediated coagulation. Data obtained shows that D-dimer was barely detectable in normal healthy mice, but was elevated by almost 50-fold at 24 h post endotoxemia. Surprisingly, at the doses that conferred a significant protection, TN markedly reduced plasma D-dimer levels by 40-50% at 24 h post endotoxemia (FIG. 12). Notably, an attenuation of the fibrinolysis may sometimes be protective, because the physical entrapment of bacteria by fibrin at the infection site may limit their capacity to spread and proliferation. Given the complex roles of fibrinolysis in sepsis, therapeutic agents that could control coagulation/fibrinolysis balance, while maintaining the host defense at the infectious foci, can be useful for understanding the complex pathogenesis of lethal systemic inflammatory diseases.

Recombinant TN protein or various truncation mutants can be generated by subcloning the cDNA corresponding to the intact mature protein (residue 1-181) or separate domains (e.g., the CRD, FIG. 1) of human or murine TN into pReceiver expression vectors downstream from a T7 promoter. After transformation of the recombinant plasmids into *E. coli* BL21 (DE3) pLysS cells, the histidine-tag-containing recombinant TN or deletion mutants are expressed and purified by the immobilized metal ion affinity chromatography as previously described in the art.

Effects of TN on the LPS-, IFN-γ-, or SAA-induced HMGB1 release. To elucidate the regulatory mechanisms of HMGB1 release, we will examine the impact of TN and its peptide agonists on the HMGB1 release induced by a wide array of inflammatory stimuli including the crude LPS [75], IFN-γ [76] and SAA [77], in macrophage and monocyte cultures. Primary peritoneal macrophages will be isolated from the Balb/C mice (both male and female, 7-8 weeks, 20-25 g) at 2-3 days after intraperitoneal injection of 2 ml thioglycollate broth (4%, Difco, Detroit, Mich.) as previously described [76,77]. Human peripheral blood mononuclear cells (HuPBMCs) will be isolated from human blood obtained from the Long Island Blood Bank (NY) by density gradient centrifugation through Ficoll as previously described [77]. At 80-90% confluence, macrophage/monocyte cultures will be stimulated with the crude LPS (Cat. No. L3012, Sigma-Aldrich), IFN-γ (Cat. No. 14777, Sigma-Aldrich), or SAA (Cat. No. 300-13, PeproTech) at different concentrations and for various time periods. The extracellular levels of HMGB1 in the culture medium will be determined by Western blotting as previously described [75-77].

Effects of TN or peptide agonist supplementation on LSI. Balb/C mice (both male and female, 7-8 weeks, 20-25 g) are subjected to lethal endotoxemia or sepsis as described above, and the recombinant TN will be injected (i.p.) at various doses and time points (2, 24, and 48 h) after the onset of endotoxemia or sepsis. Their effects on the outcomes of LSI will be assessed by comparing the long-term (two-week) survival rates between the TN-treated groups with saline vehicle-treated controls. By varying the time points (e.g., 2, 12, 24 or 36 h) when the first dose of TN will be given to animals, the therapeutic windows for the TN-based therapy will be estimated.

TN-specific peptide agonists are tested that would recapitulate the HMGB1-inhibiting capacities using both animal models of lethal endotoxemia and sepsis. Peptide agonists are given to the endotoxemic or septic mice intraperitoneally at various doses and time points after the onset of endotoxemia or sepsis. Their effects on the outcomes of LSI is assessed by comparing the long-term (two-week) survival rates between the peptide agonist groups and the saline vehicle-treated controls.

Effects of TN-neutralizing antibodies on LSI. To further validate the role of TN in LSI, TN-specific antibodies are generated in rabbits (using, e.g., a commercial vendor, Covance), and their effects tested on the outcome of LSI. The neutralizing activities of anti-TN IgGs can be determined by their impact on the TN-mediated HMGB1 inhibition or CXCL1/5 induction in vitro. Once TN-neutralizing IgGs are identified, they are then tested for possible effect on animal survival in lethal endotoxemia and sepsis. In light of the divergent roles of TN in the possible promotion of plasminogen activation [78], as well as its distinct modulation on the secretion of HMGB1 (FIG. 4) and neutrophil-attracting chemokines (e.g., CXCL1/5) (FIG. 5), it is possible that antibodies targeting different TN domains can divergently affect the outcomes of LSI. Anti-TN IgG that exhibit protective effects against LSI can be characterized by their epitopes as determined by dot blotting with a TN peptide library (18-mer offsite by 6) spanning the entire human TN protein (residues 1-181, FIG. 1). Protective anti-TN IgGs that cross-react with some peptide agonists that recapitulate TN's HMGB1-inhibiting properties are useful for management of human sepsis.

TABLE 1

Peptide agonists (From top to bottom SEQ ID NOS: 1-12, respectively.)

| Peptide | Sequence | Position | Function |
|---|---|---|---|
| P1 | LQTVCLKGT | 46-54 | Trimerization |
| P2 | KVHMKCFLAFTQTKTF | 55-70 | |
| P3 | HEASEDCISRGG | 71-83 | |
| P4 | GGTLGTPQTG | 81-90 | |
| P5 | TPQTGSENDALYEYLRQSVGNEAE | 86-109 | |
| P6 | GNEAEIWLGLNDMAAEGT | 105-122 | |
| P7 | GTWVDMTGARIAYKNWETEITAQP | 121-144 | Plasminogen binding |
| P8 | ITAQPDGGKTENC | 140-152 | Plasminogen binding |
| P9 | NCAVLSGAANGKWFDKR | 151-167 | Plasminogen binding |
| P10 | AANGKWFDKRCRDQLPYICQFGIV | 158-181 | |
| P11 | QPDGGKTENCAVLSGAANGKWFDKRCRD | 143-170 | Plasminogen binding |
| P12 | ΔTN | 45-181 | Carbohydrate recognition domain, CRD |

Example 2

Figures 13A, 13B:
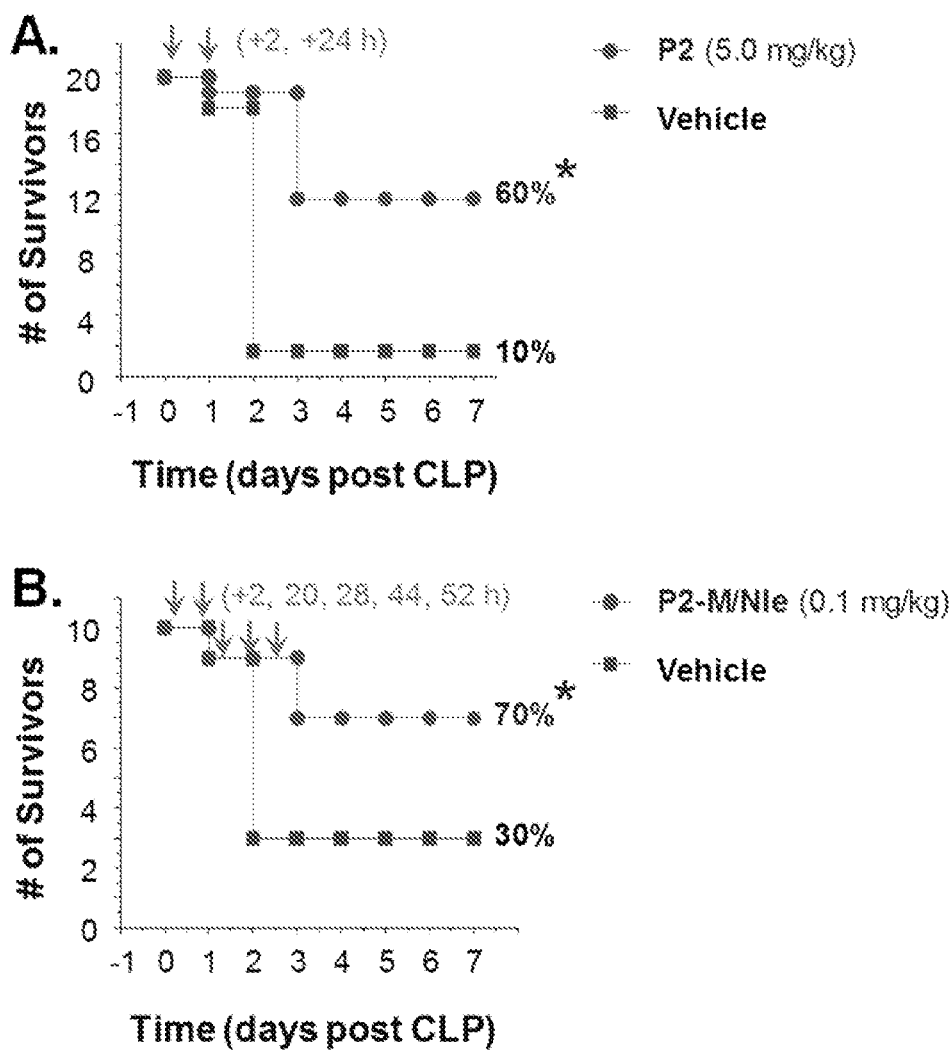
FIG. 13A-13B: Tetranectin peptide agonists (P2 and P2-M/Nle) protected mice against lethal sepsis. Male Balb/C mice were subjected to lethal sepsis by cecal ligation and puncture (CLP), and TN peptide agonist, P2 (55-KVHMKC-FLAFTQTKTF-70) (13A) (SEQ ID NO:2) or P2-M/Nle (54-TKVH(Nle)KSFLAFTQTKT-69) (13B) (SEQ ID NO:13) was given intraperitoneally at indicated dosing regimens. Animal survival rates were monitored for more than two weeks to ensure no later death. Shown was a summary of independent experiment with N=10 animals per group. The Kaplan-Meier method was used to compare the difference in mortality rates between groups. *, $P<0.05$ versus "CLP+Vehicle" group.

Two tetranectin agonist peptides were tested, one of which has an norleucine amino acid substitution from the native sequence (both are non-naturally occurring fragments of the tetranectin monomer which is typically found as an aggregate of 3 units of tetranectin and one unit of plasminogen, mediated through the trimerization domain of tetranectin). Male Balb/C mice were subjected to lethal sepsis by cecal ligation and puncture (CLP), and TN peptide agonist, P2 (55-KVHMKCFLAFTQTKTF-70) (SEQ ID NO:2) or P2-M/Nle (54-TKVH(Nle)KSFLAFTQTKT-69) (SEQ ID NO:13) was given intraperitoneally at indicated dosing regimens. Animal survival rates were monitored for more than two weeks to ensure no later death. Shown was a summary of independent experiment with N=10 animals per group. The Kaplan-Meier method was used to compare the difference in mortality rates between groups. *, P<0.05 versus "CLP+Vehicle" group. The results are shown in FIG. 13.

REFERENCES

1. Hotchkiss R S, Coopersmith C M, McDunn J E, Ferguson T A (2009) The sepsis seesaw: tilting toward immunosuppression. Nat Med 15: 496-497.
2. Riedemann N C, Guo R F, Ward P A (2003) The enigma of sepsis. J Clin Invest 112: 460-467.
3. Rittirsch D, Flierl M A, Ward P A (2008) Harmful molecular mechanisms in sepsis. Nat Rev Immunol 8: 776-787.
4. Zingarelli B (2004) Peptidoglycan is an important pathogenic factor of the inflammatory response in sepsis. Crit Care Med 32: 613-614.
5. Akira S, Takeda K (2004) Toll-like receptor signalling. Nat Rev Immunol 4: 499-511.
6. Baggiolini M, Loetscher P (2000) Chemokines in inflammation and immunity. Immunol Today 21: 418-420.
7. Balkwill F (1988) Cytokines—soluble factors in immune responses. Curr Opin Immunol 1: 241-249.
8. Poltorak A, He X, Smirnova I, Liu M Y, Huffel C V, Du X, Birdwell D, Alejos E, Silva M, Galanos C, Freudenberg M, Ricciardi-Castagnoli P, Layton B, Beutler B (1998) Defective LPS signaling in C3H/HeJ and C57BL/10ScCr mice: mutations in Tlr4 gene. Science 282: 2085-2088.

9. Wang H, Czura C. J., Tracey K. J. (2003) TNF. In: Thomson A, Lotze M T, editors. The Cytokine Handbook. Oxford: Academic Press. pp. 837-860.
10. Dinarello C A (1996) Biologic basis for interleukin-1 in disease. Blood 87: 2095-2147.
11. Heinzel F P (1990) The role of IFN-gamma in the pathology of experimental endotoxemia. J Immunol 145: 2920-2924.
12. Wang H, Bloom O, Zhang M, Vishnubhakat J M, Ombrellino M, Che J, Frazier A, Yang H, Ivanova S, Borovikova L, Manogue K R, Faist E, Abraham E, Andersson J, Andersson U, Molina P E, Abumrad N N, Sama A, Tracey K J (1999) HMG-1 as a late mediator of endotoxin lethality in mice. Science 285: 248-251.
13. Ivanov S, Dragoi A M, Wang X, Dallacosta C, Louten J, Musco G, Sitia G, Yap G S, Wan Y, Biron C A, Bianchi M E, Wang H, Chu W M (2007) A novel role for HMGB1 in TLR9-mediated inflammatory responses to CpG-DNA. Blood 110: 1970-1981.
14. Rendon-Mitchell B, Ochani M, Li J, Han J, Wang H, Yang H, Susarla S, Czura C, Mitchell R A, Chen G, Sama A E, Tracey K J, Wang H (2003) IFN-gamma Induces High Mobility Group Box 1 Protein Release Partly Through a TNF-Dependent Mechanism. J Immunol 170: 3890-3897.
15. Kim J H, Kim S J, Lee I S, Lee M S, Uematsu S, Akira S, Oh K I (2009) Bacterial endotoxin induces the release of high mobility group box 1 via the IFN-beta signaling pathway. J Immunol 182: 2458-2466.
16. Bieschke J, Russ J, Friedrich R P, Ehmhoefer D E, Wobst H, Neugebauer K, Wanker E E (2010) EGCG remodels mature alpha-synuclein and amyloid-beta fibrils and reduces cellular toxicity. Proc Natl Acad Sci USA 107: 7710-7715.
17. Li W, Zhu S, Li J, D'Amore J, D'Angelo J, Yang H, Wang P, Tracey K J, Wang H (2015) Serum Amyloid A Stimulates PKR Expression and HMGB1 Release Possibly through TLR4/RAGE Receptors. Mol Med 21: 515-525.
18. Yang D, Chen Q, Yang H, Tracey K J, Bustin M, Oppenheim J J (2007) High mobility group box-1 protein induces the migration and activation of human dendritic cells and acts as an alarmin. J Leukoc Biol 81: 59-66.
19. Dumitriu I E, Bianchi M E, Bacci M, Manfredi A A, Rovere-Querini P (2007) The secretion of HMGB1 is required for the migration of maturing dendritic cells. J Leukoc Biol 81: 84-91.
20. Orlova V V, Choi E Y, Xie C, Chavakis E, Bierhaus A, Ihanus E, Ballantyne C M, Gahmberg C G, Bianchi M E, Nawroth P P, Chavakis T (2007) A novel pathway of HMGB1-mediated inflammatory cell recruitment that requires Mac-1-integrin. EMBO J 26: 1129-1139.
21. Zhu S, Ashok M, Li J, Li W, Yang H, Wang P, Tracey K J, Sama A E, Wang H (2009) Spermine protects mice against lethal sepsis partly by attenuating surrogate inflammatory markers. Mol Med 15: 275-282.
22. Andersson U, Wang H, Palmblad K, Aveberger A C, Bloom O, Erlandsson-Harris H, Janson A, Kokkola R, Zhang M, Yang H, Tracey K J (2000) High Mobility Group 1 Protein (HMG-1) Stimulates Proinflammatory Cytokine Synthesis in Human Monocytes. J Exp Med 192: 565-570.
23. Yang H, Ochani M, Li J, Qiang X, Tanovic M, Harris H E, Susarla S M, Ulloa L, Wang H, DiRaimo R, Czura C J, Wang H, Roth J, Warren H S, Fink M P, Fenton M J, Andersson U, Tracey K J (2004) Reversing established sepsis with antagonists of endogenous high-mobility group box 1. Proc Natl Acad Sci USA 101: 296-301.
24. Wang H, Yang H, Czura C J, Sama A E, Tracey K J (2001) HMGB1 as a Late Mediator of Lethal Systemic Inflammation. Am J Respir Crit Care Med 164: 1768-1773.
25. Qin S, Wang H, Yuan R, Li H, Ochani M, Ochani K, Rosas-Ballina M, Czura C J, Huston J M, Miller E, Lin X, Sherry B, Kumar A, Larosa G, Newman W, Tracey K J, Yang H (2006) Role of HMGB1 in apoptosis-mediated sepsis lethality. J Exp Med 203: 1637-1642.
26. Wang H, Yang H, Tracey K J (2004) Extracellular role of HMGB1 in inflammation and sepsis. J Intern Med 255: 320-331.
27. Wang H, Zhu S, Zhou R, Li W, Sama A E (2008) Therapeutic potential of HMGB1-targeting agents in sepsis. Expert Rev Mol Med 10: e32.
28. Wang H, Ward M F, Sama A E (2009) Novel HMGB1-inhibiting therapeutic agents for experimental sepsis. Shock 32: 348-357.
29. Liaw P C, Ito T, Iba T, Thachil J, Zeerleder S (2016) DAMP and DIC: The role of extracellular DNA and DNA-binding proteins in the pathogenesis of DIC. Blood Rev 30: 257-261.
30. Lv B, Wang H, Tang Y, Fan Z, Xiao X, Chen F (2009) High-mobility group box 1 protein induces tissue factor expression in vascular endothelial cells via activation of NF-kappaB and Egr-1. Thromb Haemost 102: 352-359.
31. Yang X, Wang H, Zhang M, Liu J, Lv B, Chen F (2015) HMGB1: a novel protein that induced platelets active and aggregation via Toll-like receptor-4, NF-kappaB and cGMP dependent mechanisms. Diagn Pathol 10: 134.
32. Machado F R, Cesar M S (2010) Sepsis, coagulation and anticoagulants. Endocr Metab Immune Disord Drug Targets 10: 204-213.
33. Stark K, Philippi V, Stockhausen S, Busse J, Antonelli A, Miller M, Schubert I, Hoseinpour P, Chandraratne S, von Bruhl M L, Gaertner F, Lorenz M, Agresti A, Coletti R, Antoine D J, Heermann R, Jung K, Reese S, Laitinen I, Schwaiger M, Walch A, Sperandio M, Nawroth P P, Reinhardt C, Jackel S, Bianchi M E, Massberg S (2016) Disulfide HMGB1 derived from platelets coordinates venous thrombosis in mice. Blood 128: 2435-2449.
34. Ito T, Kawahara K, Nakamura T, Yamada S, Nakamura T, Abeyama K, Hashiguchi T, Maruyama I (2007) High-mobility group box 1 protein promotes development of microvascular thrombosis in rats. J Thromb Haemost 5: 109-116.
35. Hatada T, Wada H, Nobori T, Okabayashi K, Maruyama K, Abe Y, Uemoto S, Yamada S, Maruyama I (2005) Plasma concentrations and importance of High Mobility Group Box protein in the prognosis of organ failure in patients with disseminated intravascular coagulation. Thromb Haemost 94: 975-979.
36. Esmon C T (2006) Inflammation and the activated protein C anticoagulant pathway. Semin Thromb Hemost 32 Suppl 1: 49-60.
37. Levi M, van der Poll T (2010) Inflammation and coagulation. Crit Care Med 38: S26-S34.
38. Wang L, Bastarache J A, Ware L B (2008) The coagulation cascade in sepsis. Curr Pharm Des 14: 1860-1869.
39. Bernard G R, Vincent J L, Laterre P F, LaRosa S P, Dhainaut J F, Lopez-Rodriguez A, Steingrub J S, Garber G E, Helterbrand J D, Ely E W, Fisher C J J (2001) Efficacy and safety of recombinant human activated protein C for severe sepsis. N Engl J Med 344: 699-709.

40. Rosas-Ballina M, Olofsson P S, Ochani M, Valdes-Ferrer S I, Levine Y A, Reardon C, Tusche M W, Pavlov V A, Andersson U, Chavan S, Mak T W, Tracey K J (2011) Acetylcholine-synthesizing T cells relay neural signals in a vagus nerve circuit. Science 334: 98-101.
41. Borovikova L V, Ivanova S, Zhang M, Yang H, Botchkina G I, Watkins L R, Wang H, Abumrad N, Eaton J W, Tracey K J (2000) Vagus nerve stimulation attenuates the systemic inflammatory response to endotoxin. Nature 405: 458-462.
42. Wang H, Yu M, Ochani M, Amella C A, Tanovic M, Susarla S, Li J H, Wang H, Yang H, Ulloa L, Al Abed Y, Czura C J, Tracey K J (2003) Nicotinic acetylcholine receptor alpha7 subunit is an essential regulator of inflammation. Nature 421: 384-388.
43. Wang H, Liao H, Ochani M, Justiniani M, Lin X, Yang L, Al Abed Y, Wang H, Metz C, Miller E J, Tracey K J, Ulloa L (2004) Cholinergic agonists inhibit HMGB1 release and improve survival in experimental sepsis. Nat Med 10: 1216-1221.
44. Paschen W (1992) Polyamine metabolism in reversible cerebral ischemia. Cerebrovasc Brain Metab Rev 4: 59-88.
45. Zhang M, Caragine T, Wang H, Cohen P S, Botchkina G, Soda K, Bianchi M, Ulrich P, Cerami A, Sherry B, Tracey K J (1997) Spermine inhibits proinflammatory cytokine synthesis in human mononuclear cells: a counter regulatory mechanism that restrains the immune response. J Exp Med 185: 1759-1768.
46. Wang H, Zhang M, Bianchi M, Sherry B, Sama A, Tracey K J (1998) Fetuin (alpha2-HS-glycoprotein) opsonizes cationic macrophage deactivating molecules. Proc Natl Acad Sci USA 95: 14429-14434.
47. Clemmensen I, Petersen L C, Kluft C (1986) Purification and characterization of a novel, oligomeric, plasminogen kringle 4 binding protein from human plasma: tetranectin. Eur J Biochem 156: 327-333.
48. Sorensen C B, Berglund L, Petersen T E (1995) Cloning of a cDNA encoding murine tetranectin. Gene 152: 243-245.
49. Berglund L, Petersen T E (1992) The gene structure of tetranectin, a plasminogen binding protein. FEBS Lett 309: 15-19.
50. Wewer U M, Iba K, Durkin M E, Nielsen F C, Loechel F, Gilpin B J, Kuang W, Engvall E, Albrechtsen R (1998) Tetranectin is a novel marker for myogenesis during embryonic development, muscle regeneration, and muscle cell differentiation in vitro. Dev Biol 200: 247-259.
51. Christensen L, Johansen N, Jensen B A, Clemmensen I (1987) Immunohistochemical localization of a novel, human plasma protein, tetranectin, in human endocrine tissues. Histochemistry 87: 195-199.
52. Christensen L, Clemmensen I (1989) Tetranectin immunoreactivity in normal human tissues. An immunohistochemical study of exocrine epithelia and mesenchyme. Histochemistry 92: 29-35.
53. Jensen B A, McNair P, Hyldstrup L, Clemmensen I (1987) Plasma tetranectin in healthy male and female individuals, measured by enzyme-linked immunosorbent assay. J Lab Clin Med 110: 612-617.
54. Kluft C, Los P, Clemmensen I (1989) Calcium-dependent binding of tetranectin to fibrin. Thromb Res 55: 233-238.
55. Lorentsen R H, Graversen J H, Caterer N R, Thogersen H C, Etzerodt M (2000) The heparin-binding site in tetranectin is located in the N-terminal region and binding does not involve the carbohydrate recognition domain. Biochem J 347 Pt 1: 83-87.
56. Graversen J H, Lorentsen R H, Jacobsen C, Moestrup S K, Sigurskjold B W, Thogersen H C, Etzerodt M (1998) The plasminogen binding site of the C-type lectin tetranectin is located in the carbohydrate recognition domain, and binding is sensitive to both calcium and lysine. J Biol Chem 273: 29241-29246.
57. Graversen J H, Sigurskjold B W, Thogersen H C, Etzerodt M (2000) Tetranectin-binding site on plasminogen kringle 4 involves the lysine-binding pocket and at least one additional amino acid residue. Biochemistry 39: 7414-7419.
58. Kluft C, Jie A F, Los P, de W E, Havekes L (1989) Functional analogy between lipoprotein(a) and plasminogen in the binding to the kringle 4 binding protein, tetranectin. Biochem Biophys Res Commun 161: 427-433.
59. Westergaard U B, Andersen M H, Heegaard C W, Fedosov S N, Petersen T E (2003) Tetranectin binds hepatocyte growth factor and tissue-type plasminogen activator. Eur J Biochem 270: 1850-1854.
60. Wewer U M, Ibaraki K, Schjorring P, Durkin M E, Young M F, Albrechtsen R (1994) A potential role for tetranectin in mineralization during osteogenesis. J Cell Biol 127: 1767-1775.
61. Iba K, Durkin M E, Johnsen L, Hunziker E, Damgaard-Pedersen K, Zhang H, Engvall E, Albrechtsen R, Wewer U M (2001) Mice with a targeted deletion of the tetranectin gene exhibit a spinal deformity. Mol Cell Biol 21: 7817-7825.
62. Wang E S, Zhang X P, Yao H B, Wang G, Chen S W, Gao W W, Yao H J, Sun Y R, Xi C H, Ji Y D (2014) Tetranectin knockout mice develop features of Parkinson disease. Cell Physiol Biochem 34: 277-287.
63. Iba K, Hatakeyama N, Kojima T, Murata M, Matsumura T, Wewer U M, Wada T, Sawada N, Yamashita T (2009) Impaired cutaneous wound healing in mice lacking tetranectin. Wound Repair Regen 17: 108-112.
64. Iba K, Abe Y, Chikenji T, Kanaya K, Chiba H, Sasaki K, Dohke T, Wada T, Yamashita T (2013) Delayed fracture healing in tetranectin-deficient mice. J Bone Miner Metab 31: 399-408.
65. Levy M M, Fink M P, Marshall J C, Abraham E, Angus D, Cook D, Cohen J, Opal S M, Vincent J L, Ramsay G (2003) 2001 SCCM/ESICM/ACCP/ATS/SIS International Sepsis Definitions Conference. Crit Care Med 31: 1250-1256.
66. Wewer U M, Iba K, Durkin M E, Nielsen F C, Loechel F, Gilpin B J, Kuang W, Engvall E, Albrechtsen R (1998) Tetranectin is a novel marker for myogenesis during embryonic development, muscle regeneration, and muscle cell differentiation in vitro. Dev Biol 200: 247-259.
67. Shea-Donohue T, Thomas K, Cody M J, Aiping Z, Detolla L J, Kopydlowski K M, Fukata M, Lira S A, Vogel S N (2008) Mice deficient in the CXCR2 ligand, CXCL1 (KC/GRO-alpha), exhibit increased susceptibility to dextran sodium sulfate (DSS)-induced colitis. Innate Immun 14: 117-124.
68. Jin L, Batra S, Douda D N, Palaniyar N, Jeyaseelan S (2014) CXCL1 contributes to host defense in polymicrobial sepsis via modulating T cell and neutrophil functions. J Immunol 193: 3549-3558.
69. Jeyaseelan S, Manzer R, Young S K, Yamamoto M, Akira S, Mason R J, Worthen G S (2005) Induction of CXCL5 during inflammation in the rodent lung involves activation of alveolar epithelium. Am J Respir Cell Mol Biol 32: 531-539.
70. Mei J, Liu Y, Dai N, Favara M, Greene T, Jeyaseelan S, Poncz M, Lee J S, Worthen G S (2010) CXCL5 regulates chemokine scavenging and pulmonary host defense to bacterial infection. Immunity 33: 106-117.
71. Zhang Y, Li W, Zhu S, Jundoria A, Li J, Yang H, Fan S, Wang P, Tracey K J, Sama A E, Wang H (2012) Tanshinone IIA sodium sulfonate facilitates endocytic HMGB1 uptake. Biochem Pharmacol 84: 1492-1500.
72. Yang H, Wang H, Levine Y A, Gunasekaran M K, Wang Y, Addorisio M, Zhu S, Li W, Li J, de Kleijn D P, Olofsson P S, Warren H S, He M, Al-Abed Y, Roth J, Antoine D J, Chavan S S, Andersson U, Tracey K J (2016) Identification of CD163 as an antiinflammatory receptor for HMGB1-haptoglobin complexes. JCI Insight 1.
73. Yang H, Hreggvidsdottir H S, Palmblad K, Wang H, Ochani M, Li J, Lu B, Chavan S, Rosas-Ballina M, Al Abed Y, Akira S, Bierhaus A, Erlandsson-Harris H, Andersson U, Tracey K J (2010) A critical cysteine is required for HMGB1 binding to Toll-like receptor 4 and activation of macrophage cytokine release. Proc Natl Acad Sci USA 107: 11942-11947.
74. Graversen J H, Sigurskjold B W, Thogersen H C, Etzerodt M (2000) Tetranectin-binding site on plasminogen kringle 4 involves the lysine-binding pocket and at least one additional amino acid residue. Biochemistry 39: 7414-7419.
75. Wang H, Bloom O, Zhang M, Vishnubhakat J M, Ombrellino M, Che J, Frazier A, Yang H, Ivanova S, Borovikova L, Manogue K R, Faist E, Abraham E, Andersson J, Andersson U, Molina P E, Abumrad N N, Sama A, Tracey K J (1999) HMG-1 as a late mediator of endotoxin lethality in mice. Science 285: 248-251.
76. Rendon-Mitchell B, Ochani M, Li J, Han J, Wang H, Yang H, Susarla S, Czura C, Mitchell R A, Chen G, Sama A E, Tracey K J, Wang H (2003) IFN-gamma Induces High Mobility Group Box 1 Protein Release Partly Through a TNF-Dependent Mechanism. J Immunol 170: 3890-3897.
77. Li W, Zhu S, Li J, Yang H, Tracey K. J., Wang P, Sama A E, Wang H (2014) Characterization of human SAA, but not SAA1, as a positive regulator of HMGB1 release. Shock 41: 46-47.
78. Westergaard U B, Andersen M H, Heegaard C W, Fedosov S N, Petersen T E (2003) Tetranectin binds hepatocyte growth factor and tissue-type plasminogen activator. Eur J Biochem 270: 1850-1854.

What is claimed is:

1. A method of treating endotoxemia or sepsis in a subject, or reducing likelihood of death therefrom, comprising administering to the subject having endotoxemia or sepsis an amount of a tetranectin protein, or a tetranectin peptide agonist, effective to treat endotoxemia or sepsis in the subject, wherein the tetranectin protein has the amino acid sequence of a human tetranectin protein;
   or wherein the tetranectin peptide agonist comprises the amino acid sequence TKVH(Nle)KSFLAFTQTKT (SEQ ID NO:13);
   and wherein neither the tetranectin protein nor the tetranectin peptide agonist is isolated from, or produced in, a human.

2. A method of reducing development of sepsis-associated coagulation or development of fibrinolysis in a subject comprising administering to the subject an amount of tetranectin protein or a tetranectin peptide agonist effective to reduce the development of sepsis-associated coagulation or development of fibrinolysis in the subject, wherein the tetranectin protein has the sequence of a human tetranectin protein but is not isolated from, or produced in, a human, or wherein the tetranectin peptide agonist comprises TKVH(Nle)KSFLAFTQTKT (SEQ ID NO:13).

3. The method of claim 1, wherein the subject is a human subject.

4. The method of claim 3, wherein the subject is 60 years or older, or is immunocompromised.

5. The method of claim 1, wherein the amount of tetranectin protein is administered and the tetranectin protein is a recombinantly produced tetranectin protein.

6. The method of claim 1, wherein the amount of tetranectin protein is administered.

7. The method of claim 1, wherein the tetranectin peptide agonist comprises a sequence of a plasminogen-binding region of a tetranectin protein.

8. The method of claim 1, further comprising one or more additional administration(s) of an amount of tetranectin protein or of tetranectin peptide agonist subsequent to the first administration.

9. The method of claim 1, wherein the tetranectin peptide agonist comprising TKVH(Nle)KSFLAFTQTKT (SEQ ID NO:13) is administered.

10. A tetranectin peptide agonist composition comprising a peptide comprising TKVH(Nle)KSFLAFTQTKT (SEQ ID NO:13).

11. The tetranectin peptide agonist composition of claim 10 comprising a pharmaceutically acceptable carrier.

* * * * *